United States Patent
Guerin et al.

(10) Patent No.: US 12,252,490 B2
(45) Date of Patent: Mar. 18, 2025

(54) INHIBITING DEUBIQUITINASE USP25 AND USP28

(71) Applicant: Valo Health, Inc., Lexington, MA (US)

(72) Inventors: David J. Guerin, Natick, MA (US); Justin A. Caravella, Cambridge, MA (US); Hongbin Li, Madison, CT (US); Steven Mischke, Waltham, MA (US); David J. Richard, Littleton, MA (US); Shawn E. R. Schiller, Haverhill, MA (US); Tatiana Shelekhin, Ridgefield, CT (US)

(73) Assignee: Valo Health, Inc., Lexington, MA (US)

( * ) Notice: Subject to any disclaimer, the term of this patent is extended or adjusted under 35 U.S.C. 154(b) by 796 days.

(21) Appl. No.: 17/265,883

(22) PCT Filed: Aug. 8, 2019

(86) PCT No.: PCT/US2019/045734
§ 371 (c)(1),
(2) Date: Feb. 4, 2021

(87) PCT Pub. No.: WO2020/033709
PCT Pub. Date: Feb. 13, 2020

(65) Prior Publication Data
US 2021/0179628 A1    Jun. 17, 2021

Related U.S. Application Data

(60) Provisional application No. 62/716,738, filed on Aug. 9, 2018.

(51) Int. Cl.
| | | |
|---|---|---|
| C07D 487/04 | (2006.01) | |
| A61P 35/00 | (2006.01) | |
| C07D 471/04 | (2006.01) | |
| C07D 487/08 | (2006.01) | |
| C07D 519/00 | (2006.01) | |

(52) U.S. Cl.
CPC ......... C07D 487/04 (2013.01); C07D 471/04 (2013.01); C07D 519/00 (2013.01)

(58) Field of Classification Search
CPC .. C07D 487/04; C07D 471/04; C07D 519/00; C07D 487/08; A61P 35/00
See application file for complete search history.

(56) References Cited

U.S. PATENT DOCUMENTS

| | | |
|---|---|---|
| 10,889,592 B2 | 1/2021 | Guerin et al. |
| 10,913,753 B2 | 2/2021 | Guerin et al. |
| 11,130,748 B2 | 9/2021 | Kemp et al. |
| 2021/0047343 A1 | 2/2021 | Guerin et al. |

FOREIGN PATENT DOCUMENTS

| | | | |
|---|---|---|---|
| CA | 2958262 A1 | 3/2016 | |
| CN | 108368089 A | 8/2018 | |
| WO | WO 2000/078934 | 12/2000 | |
| WO | WO 2005/037845 | 4/2004 | |
| WO | WO 2006/068618 | 6/2006 | |
| WO | WO 2010/099166 | 9/2010 | |
| WO | WO 2012/040527 | 3/2012 | |
| WO | WO 2014/105952 | 7/2014 | |
| WO | WO 2014//116859 | 7/2014 | |
| WO | WO 2017/139778 | 8/2017 | |
| WO | WO 2017/139779 | 8/2017 | |
| WO | WO-2017139778 A1 * | 8/2017 | ............... A61P 29/00 |
| WO | WO-2017139779 A1 * | 8/2017 | ............... A61P 35/00 |
| WO | WO 2019/032863 | 2/2019 | |
| WO | WO 2020/033707 | 2/2020 | |
| WO | WO 2010/092153 | 8/2020 | |

OTHER PUBLICATIONS

Beroukhim et al., "The landscape of somatic copy-number alteration across human cancers,"Nature vol. 463, doi.10.1038/nature08822, pp. 899-905, (2010).
Bradley et al., "Tumor necrosis factor receptor-associated factors (TRAFs),"Oncogene Nature 20, pp. 6482-6491, (2001).
Brockman et al., "Small Molecule Inhibitors of Aurora-A Induce Proteasomal Degradation of N-Myc in Childhood Neuroblastoma" Cancer Cell., 24(1), Doi:10.1016/.ccr.2013.05.005, pp. 75-89, (2013).
Colland et al., "Small-molecule inhibitor of USP7/HAUSP ubiquitin protease stabilizes and activates p53 in cells," Molecular Cancer Therapeutics, DOI: 10.1158-1535-7163.MCT-09-0097, pp. 2286-2295, (2009).

(Continued)

*Primary Examiner* — James H Alstrum-Acevedo
*Assistant Examiner* — Chantal Adlam
(74) *Attorney, Agent, or Firm* — Barnes & Thornburg LLP; Aisha R. Hasan; Ryan L. Marshall

(57) ABSTRACT

The present disclosure relates to modulators, such as inhibitors, of at least one pathway chosen from USP28 and USP25, pharmaceutical compositions comprising the inhibitors, and methods of using the inhibitors. The modulators, such as inhibitors, of at least one pathway chosen from USP28 and USP25 can be useful in the treatment of cancers, among other ailments. The present disclosure provides compounds of Formula (I).

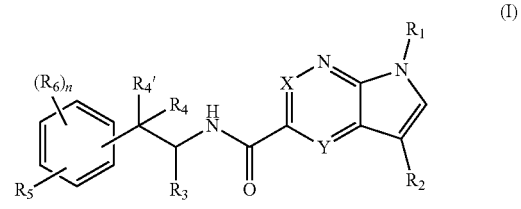

15 Claims, No Drawings

(56) References Cited

OTHER PUBLICATIONS

Colombo et al., "Synthesis and biological evaluation of 9-oxo-9H-indeno[1,2-b]pyrazine-2,3-dicarbonitrile Analogues as Potential Inhibitors of Deubiquitinating Enzymes," ChemMedChem DOI: 10.1002/cmdc.200900409, pp. 552-558, (2010).
Conacci-Sorrell et al., "An Overview of MYC and Its Interactome," Cold Spring Harb Perspect Med 2014;4:a014357, pp. 1-24 (2014).
Cremona et al., "Fbw7 and Its Counteracting Forces in Stem Cells and Cancer: Oncoproteins in the Balance," Semin Cancer Biol., 36:52-61, Feb. 2016.
Cui et al., "Mechanisms and pathways of innate immune activation and regulation in health and cancer," Human Vaccines & Immunotherapeutics 10:11, pp. 3270-3285, (2014).
D'Arcy et al., "Deubiquitinase inhibition as a cancer therapeutic strategy," Pharmacology & Therapeutics 147, http://dx.doi.org/10.1016/j.pharmthera.2014.11.002, pp. 32-54, (2015).
Diefenbacher et al., "The deubiquitinase USPZS controls intestinal homeostasis and promotes colorectal cancer," The Journal of Clinical Investigation, vol. 124, No. 8 doi:10.1172/JCI73733, pp. 3407-3418 (2014).
Diefenbacher et al., "Usp28 Counteracts Fbw7 in Intestinal Homeostasis and Cancer," Cancer Res., 75(7):1181-6, Apr. 1, 2015. (Epub Feb. 25, 2015)
Examination Report issued in European Patent Application No. 17708031.4, dated Jun. 13, 2019.
Farshi et al., "Deubiquitinases (DUBs) and DUB inhibitors: a patent review," Expert Opin Ther Pat., 25(10):1191-1208, 2015.
Flugel et al., "GSK-SB regulates cell growth, migration, and angiogenesis via Fbw7 and USP28-dependent degradation of HIF-1a," Vascular Biology, Blood, vol. 119, No. 5, pp. 1292-1301, (2012).
Gabay et al., "MYC Activation is a Hallmark of Cancer Initiation and Maintenance," Cold Spring Harb Perspect Med 2014;4:a014241, pp. 1-13 (2014).
Gersch et al., "Distinct USP25 and USPZS Oligomerization States Regulate Deubiquitinating Activity," Mol. Cell 74:436-451, May 2, 2019.
Guo et al., "USP28 is a potential prognostic marker for bladder cancer," Tumor Biology DOI 10.1007/513277-013-1525-1, pp. 4017-4022 (2013).
Huang et al., "euroblastoma and MYCN," Cold Spring Harb Perspect Med 2013;3:a014415; pp. 1-22, (2013).
International Search Report and Written Opinion for International Application No. PCT/US2017/017690, pp. 1-11, Apr. 19, 2017.
International Search Report and Written Opinion for International Application No. PCT/US2017/017691, pp. 1-6, Mar. 29, 2017.
International Search Report issued in Application No. PCT/US2018/046061, dated Oct. 25, 2018.
International Search Report issued in Application No. PCT/US2019/045732, dated Oct. 23, 2019.
International Search Report issued in Application No. PCT/US2019/045734, dated Jan. 2, 2020.
Iwakura et al., "Functional Specialization of Interleukin-17 Family Members," Immunity 34, pp. 149-162 (2011).
Kapuria et al., "Deubiquitinase Inhibition by Small-Molecule WP1130 Triggers Aggresome Formation and Tumor Cell Apoptosis," Cancer Research Therapeutics, Targets, and Chemical Biology DOI: 10.1158/0008-5472.CAN-10-1530, pp. 9265-9276, (2010).
Knobel et al., "USP28 Is Recruited to Sites of DNA Damage by the Tandem BRCT Domains of 53BP1 but Plays a Minor Role in Double-Strand Break Metabolism," Molecular and Cellular Biology, vol. 34, No. 11, pp. 2062-2074 (2014).
Komander et al., "Breaking the chains: structure and function of the deubiquitinases," Nature, vol. 10, pp. 550-563 (2009).
Le et al., "Discovery of a selective M4 positive allosteric modulator based on the 3-amino-thieno[2,3-b]pyridine-2-carboxamide scaffold: development of ML253, a potent and brain penetrant compound that is active in a preclinical model of schizophrenia," Bioorg Med Chem Lett. doi:10.1016/j.bmcl.2012.10.073, pp. 346-350 (2013).
Lee et al., "Enhancement of proteasome activity by a small-molecule inhibitor of USP14," Nature 467 doi:10.1038/nature09299, pp. 179-184 (2010).
Li et al., "miRNA-200c inhibits invasion and metastasis of human non-small cell lung cancer by directly targeting ubiquitin specific peptidase 25," Molecular Cancer, vol. 13, pp. 1-14 (2014).
Liang et al., "A selective USP1-UAF1 inhibitor links deubiquitination to DNA damage responses," Nat. Chem. Biol. DOI: 10.1038/NCHEMBIO.1455, pp. 298-304 (2014).
Lorenzin et al., "Different promoter affinities account for specificity in MYC-dependent gene regulation," eLife 2016;5:e15161, pp. 1-35 (2016).
Meng et al., "γ-Secretase Inhibitors Abrogate Oxaliplatin-Induced Activation of the Notch-1 Signaling Pathway in Colon Cancer Cells Resulting in Enhanced Chemosensitivity," Cancer Research 69(2), pp. 573-582 (2009).
Metzger et al., "LSD1 demethylates repressive histone marks to promote androgen-receptor-dependent transcription," Nature doi:10.1038/nature04020, vol. 437, pp. 436-439 (2005).
Meyer et al. "Reflecting on 25 years with MYC," Nature Perspectives, vol. 8, pp. 976-990 (2008).
Nijman et al., "A Genomic and Functional Inventory of Deubiquitinating Enzymes,"Cell 123, pp. 773-786 (2005).
Periz et al., "Regulation of Protein Quality Control by UBE4B and LSD1 through p53-Mediated Transcription," PLOS Biology DOI:10.1371/journal.pbio.1002114, pp. 1-29 (2015).
Popov et al., "The ubiquitin-specific protease USP28 is required for MYC stability," Nature Cell Biology, vol. 9, No. 7, pp. 765-774 (2007).
Popov et al., "Fbw7 and Usp28 Regulate Myc Protein Stability in Response to DNA Damage," Cell Cycle, 6:19, 2327-2331, Oct. 2, 2007.
Prieto-Garcia et al., "The USP28-ΔNp63 axis is a vulnerability of squamous tumours," bioRxiv preprint, Jun. 27, 2019.
Reverdy et al., "Discovery of Specific Inhibitors of Human USP7/HAUSP Deubiquitinating Enzyme," Chemistry & Biology 19, pp. 467-477 + Supplemental Information, (2012).
Roussel et al., "Role of MYC in Medulloblastoma," Cold Spring Harb Perspect Med 2013;3:a014308; pp. 1-15, (2013).
Sacco et al., "Emerging Roles of Deubiquitinases in Cancer-Associated Pathways," Life 62(2):140-157, Feb. 2010.
Sankar et al., "Reversible LSD1 Inhibition Interferes with Global EWS/ETS Transcriptional Activity and Impedes Ewing Sarcoma Tumor Growth," Clinical Cancer Research, DOI: 10.1158/1078-0432.CCR-14-0072, pp. 4584-4597 (2014).
Sauer et al., "Differential Oligomerization of the Deubiquitinases USP25 and USP28 Regulates Their Activities," Mol. Cell 74(3):421-435, May 2, 2019.
Schenk et al., "Inhibition of the LSD1 (KDM1A) demethylase reactivates the all-trans-retinoic acid differentiation pathway in acute myeloid leukemia," Nature Medicine, vol. 18, No. 4, pp. 605-611 (2012).
Schmitz et al., "Oncogenic Mechanisms in Burkitt Lymphoma," Cold Spring Harb Perspect Med 2014;4:a014282, pp. 1-13 (2014).
Schulein-Volk et al., "Dual Regulation of Fbw7 Function and Oncogenic Transformation b Usp28," Cell Reports 9, 1099-1109, Nov. 6, 2014.
Sheridan, C., "Drug makers target ubiquitin proteasome pathway anew," Nature Biotechnology, vol. 33, No. 11, pp. 1115-1117 (2015); corrected version (2016).
Stoeck et al., "Discovery of Biomarkers Predictive of GSI Response in Triple-Negative Breast Cancer and Adenoid Cystic Carcinoma,"American Association for Cancer Research, Cancer Discovery DOI: 10.1158/2159-8290.CD-13-0830, pp. 1155-1167 (2014).
Toffolo et al., "Phosphorylation of neuronal Lysine-Specific Demethylase 1LSD1/KDM1A impairs transcriptional repression by regulating interaction with CoREST and histone deacetylases HDAC1/2," Journal of Neurochemistry, vol. 128, doi: 10.1111/jnc.12457, pp. 603-616 (2014).

(56) References Cited

OTHER PUBLICATIONS

Walsh et al., "Tumor necrosis factor receptor-associated factor 6 (TRAF6) regulation of development, function, and homeostasis of the immune system," John Wiley & Sons Ltd, Immunological Reviews 0105-2896, vol. 266, pp. 72-92 (2015).

Walz et al., "Activation and repression by oncogenic MYC shape tumour-specific gene expression profiles," Nature, doi:10.1038/nature13473, pp. 1-17 (2014).

Wang et al., "Ubiquitin-specific protease 28 is overexpressed in human glioblastomas and contributes to glioma tumorigenicity by regulating MYC expression," Experimental Biology and Medicine, DOI: 10.1177/1535370215595468, pp. 255-264 (2015).

Weng et al., "Activating Mutations of NOTCH1 in Human T Cell Acute Lymphoblastic Leukemia," Science, vol. 306, pp. 269-271 (2004).

Wrigley et al., "Enzymatic characterisation of USP7 deubiquitinating activity and inhibition," Cell Biochem. Biophys., vol. 60, DOI 10.1007/512013-011-9186-4, pp. 99-111 (2011).

Wrigley et al., "Identification and Characterization of Dual Inhibitors of the USP25/28 Deubiquitinating Enzyme Subfamily" ACS Chem. Biol. 12, pp. 3113-3125 (2017).

Wrigley et al., "Identification and Characterization of Dual Inhibitors of the USP25/28 Deubiquitinating Enzyme Subfamily," Peer-reviewed (pre-print) version, published Nov. 13, 2017.

Wu et al., "The Deubiquitinase USP28 Stabilizes LSD1 and Confers Stem-Cell-like Traits to Breast Cancer Cells," Cell Press Reports, vol. 5, pp. 224-236 (2013).

Zhang et al., "A Role for the Deubiquitinating EnzymeUSP28 in Control of the DNA-Damage Response," Cell 126, pp.s 529-542 (2006).

Zhang et al., "Overexpression of deubiquitinating enzyme USP28 promoted non-small cell lung cancer growth," J. Cell Mol. Med., pp. 1-7 , doi: 10.1111/jcmm.12426 (2015).

Zhong et al., "Negative regulation of IL-17-mediated signaling and inflammation by the ubiquitin-specific protease USP28," Nature Immunology, vol. 13, No. 11, pp. 1110-1117 (2012).

Zhong et al., "Ubiquitin-Specific Protease 25 Regulates TLR4-Dependent Innate Immune Responses Through Deubiquitination of the Adaptor Protein TRAF3," Science Signaling, vol. 6, Issue 275 ra35, pp. 1-10 (2013).

Zhong et al., "Ubiquitin-Specific Proteases 25 Negatively Regulates Virus-Induced Type I Interferon Signaling," PLOS One, vol. 8, Issue 11, pp. 1-14 (2013).

Valero R. "Characterization of alternatively spliced products and tissue-specific isoforms of USP28 and USP25", Genome biology, Dec. 31, 2001, vol. 2, No. 2.

Wang et al., "New Advances in the Study on Deubiquitinating Enzymes in Breast Cancer Research", *Progress in Modern Biomedicine*, 03, Feb. 15, 2018.

Search Report, Chinese Application No. 2019800664709, Feb. 15, 2023, 2 pages.

* cited by examiner

INHIBITING DEUBIQUITINASE USP25 AND USP28

CROSS REFERENCE TO RELATED APPLICATION

This application is a National Stage application of International Application No. PCT/US2019/045734, filed Aug. 8, 2019, which claims the benefit of U.S. Provisional Application No. 62/716,738, filed Aug. 9, 2018.

TECHNICAL FIELD

The present disclosure relates to the inhibition of ubiquitin-specific protease 28 (USP28) and/or ubiquitin-specific protease 25 (USP25) using novel chemical compounds.

BACKGROUND

USP28 and USP25 play roles in the deubiquitination and stabilization of diverse oncoproteins and epigenetic drivers and immunomodulatory proteins among other cellular factors, which relate to immune responses and tumor initiation and growth in humans. Inhibition of USP28 and/or USP25 with small molecule inhibitors therefore can be developed for medical use, such as for the treatment for cancer, such as lung cancer. For this reason, there remains a considerable need for novel and potent small molecule inhibitors of USP28 and/or USP25.

SUMMARY

The present disclosure provides compounds of Formula (I):

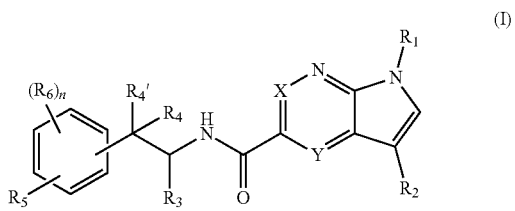

and pharmaceutically acceptable forms thereof, wherein:
X is selected from N or C(R');
R' is selected from hydrogen, deuterium, and $CH_3$;
Y is C(R);
R is selected from hydrogen, $NH_2$, and C1-C4 alkyl groups;
$R_1$ is selected from Rx, hydrogen, C1-C5 linear and C3-C5 branched alkyl groups, wherein the alkyl groups are optionally substituted with one or more Rx;
Rx is selected from small lipophilic and/or electron withdrawing groups that exhibit activity in a USP28 and/or USP25 biochemical assay,
$R_2$ is selected from hydrogen and halogens;
$R_3$, $R_4$, and $R_4'$ are each independently selected from hydrogen, and C1-C4 alkyl groups;
$R_5$ is selected 6- to 8-membered heterocyclic rings;
$R_6$ is selected from hydrogen, deuterium, halogens, C1-C4 alkyl, and —CN; and
n is 0, 1, or 2.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

DESCRIPTION OF THE EMBODIMENTS

Compounds useful for inhibiting USP 28 and/or USP25 are disclosed herein, including USP25 Inhibitor compounds, USP28 Inhibitor compounds and USP28/25 Inhibitor compounds as defined herein. The USP28/25 Inhibitor, USP28 Inhibitor and/or USP25 Inhibitor compounds can be a compound disclosed herein, including a compound of Formula (I).

The term "USP28 Inhibitor" as used herein refers to a compound disclosed herein (e.g., a compound of Formula (I)) having an $IC_{50}$ of 10 micromolar or less in the Ubiquitin-Rhodamine 110 Assay for USP28 as described in Example A-1(a) and/or A-1(b) herein. For example, the USP28 Inhibitor can be a compound of a formula disclosed herein having an $IC_{50}$ value of up to 10 micromolar using the Ubiquitin-Rhodamine 110 Assay for USP28 as described in Example A-1(a), including $IC_{50}$ values ranging from 0.001-10 micromolar, such as ranging from 0.001-2 micromolar, preferably 0.001-0.2 micromolar, more preferably 0.001-0.05 micromolar. The USP28 Inhibitor can be a compound of a formula disclosed herein having an $IC_{50}$ value of up to 10 micromolar using the Ubiquitin-Rhodamine 110 Assay for USP28 as described in Example A-1(b), including $IC_{50}$ values ranging from 0.001-10 micromolar, such as ranging from 0.001-2 micromolar, preferably 0.001-0.2 micromolar, more preferably from 0.001-0.05 micromolar. The USP28 Inhibitor can be a compound of a formula disclosed herein having an $IC_{50}$ value of up to 10 micromolar using both the Ubiquitin-Rhodamine 110 Assay for USP28 as described in Example A-1(a) and the Ubiquitin-Rhodamine 110 Assay for USP28 as described in Example A-1(b), including $IC_{50}$ values of 0.001-10 micromolar, such as ranging from 0.001-2 micromolar, preferably 0.001-0.2 micromolar, more preferably 0.001-0.05 micromolar for both assays.

The term "USP25 Inhibitor" as used herein refers to a compound disclosed herein (e.g., a compound of Formula (I)) having an $IC_{50}$ of 10 micromolar or less in the Ubiquitin-Rhodamine 110 Assay for USP25 as described in Example A-2 herein. For example, the USP25 Inhibitor can be a compound of a formula disclosed herein having an $IC_{50}$ value of up to 10 micromolar using the Ubiquitin-Rhodamine 110 Assay for USP25 as described in Example A-2, including $IC_{50}$ values ranging from 0.001-10 micromolar, such as ranging from 0.001-2 micromolar, preferably 0.001-0.2 micromolar, more preferably 0.001-0.05 micromolar.

The term "USP28/25 Inhibitor" as used herein refers to a compound disclosed herein (e.g., a compound of Formula (I)) that is a USP28 Inhibitor or a USP25 Inhibitor or both a USP28 Inhibitor and USP25 Inhibitor, as defined herein.

Optionally, any one or more hydrogen atoms in a compound of Formula (I) can independently be replaced with deuterium or other hydrogen isotope.

As noted above and below, the present disclosure relates to compounds of formula (I):

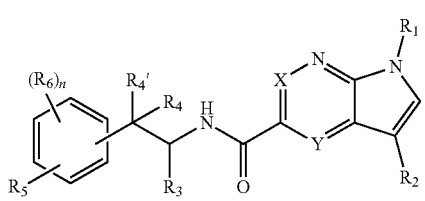

and pharmaceutically acceptable forms thereof, wherein:
X, Y, R, R', Rx, $R_1$, $R_2$, $R_3$, $R_4$, $R_4'$, $R_5$, $R_6$ and n are all as defined above.

In at least one embodiment, X is N. In at least one embodiment, X is C(R'), wherein R is hydrogen. In at least one embodiment, X is C(R'), wherein R is $CH_3$. In preferred embodiments X is CH.

In at least one embodiment, Y is CH. In at least one embodiment, Y is C—$NH_2$.

In at least one embodiment, Rx is selected from halogens, deuterium, —OH.

In at least one embodiment, $R_1$ is selected from hydrogen. In at least one embodiment, $R_1$ is selected from linear or branched alkyl groups, which are optionally substituted with one or more Rx. In at least one embodiment, $R_1$ is selected from branched alkyl groups substituted with Rx, wherein Rx is selected from halogens and —OH groups.

In at least one embodiment, $R_2$ is selected from hydrogen. In at least one embodiment, $R_2$ is selected from halogens.

In at least one embodiment, $R_3$, $R_4$, and $R_4'$ are each hydrogen. In at least one embodiment, $R_3$ is hydrogen, and one of $R_4$ and $R_4'$ is hydrogen while the other is selected from C1-C4 alkyl groups. In at least one embodiment, $R_3$ is hydrogen, and one of $R_4$ and $R_4'$ is hydrogen while the other is $CH_3$.

In at least one embodiment, $R_5$ is selected from 6-membered heterocyclic rings. In at least one embodiment, $R_5$ is selected from 7-membered heterocyclic rings. In preferred embodiments, the heterocyclic rings have two nitrogens.

In at least one embodiment, $R_6$ is selected from hydrogen. In at least one embodiment, $R_6$ is selected from halogens. In preferred embodiments the halogens are selected from F and Cl.

In at least one embodiment, n is 0. In at least one embodiment n is 1. In at least one embodiment n is 2.

In at least one embodiment, the compounds of Formula (I) are chosen from compounds wherein X is C(R'); R' is selected from hydrogen and deuterium; R is $NH_2$; $R_1$, $R_2$, $R_3$, $R_4$, and $R_4'$ are hydrogen; $R_5$ is selected from 6-membered heterocyclic rings, and n is 0.

In at least one embodiment, the compounds of Formula (I) are chosen from compounds wherein X is C(R'); R' is selected from hydrogen and deuterium; R is hydrogen; $R_1$ is chosen from C1-C3 linear alkyl groups optionally substituted with one to three Rx; Rx is selected from halogens, and —OH; $R_2$ and $R_3$ are hydrogen; $R_4$, and $R_4'$ are selected from hydrogen and $CH_3$; $R_5$ is selected from 6-8-membered heterocyclic rings; $R_6$ is selected from hydrogen, deuterium, and halogens; and n is 0, 1, or 2.

In at least one embodiment, the compounds of Formula (I) are chosen from compounds wherein X is C(R'); R' is selected from hydrogen; R is hydrogen; $R_1$ is chosen from methyl and ethyl groups optionally substituted with one to three Rx; Rx is selected from halogens, and —OH; $R_2$ and $R_3$ are hydrogen; $R_4$, and $R_4'$ are selected from hydrogen and $CH_3$; $R_5$ is selected from 6-8-membered heterocyclic rings; $R_6$ is selected from hydrogen and halogens; and n is 0, 1, or 2.

In at least one embodiment, the compounds of Formula (I) are chosen from compounds wherein X is C(R'); R' is selected from hydrogen and deuterium; R is hydrogen; $R_1$ is chosen from C3-C4 branched alkyl groups optionally substituted with one to three Rx; Rx is selected from halogens, and —OH; $R_2$ and $R_3$ are hydrogen; $R_4$, and $R_4'$ are selected from hydrogen and $CH_3$; $R_5$ is selected from 6-8-membered heterocyclic rings; $R_6$ is selected from hydrogen, deuterium, and halogens; and n is 0, 1, or 2.

In at least one embodiment, the compounds of Formula (I) are chosen from compounds wherein X is C(R'); R' is selected from hydrogen; R is hydrogen; $R_1$ is chosen from C3-C4 branched alkyl groups optionally substituted with one to three Rx; Rx is selected from halogens, and —OH; $R_2$ and $R_3$ are hydrogen; $R_4$, and $R_4'$ are selected from hydrogen; $R_5$ is selected from 6-8-membered heterocyclic rings; $R_6$ is selected from hydrogen, and halogens; and n is 0, 1, or 2.

In at least one embodiment, the compounds of Formula (I) are chosen from compounds wherein X is C(R'); R' is selected from hydrogen; R is hydrogen; $R_1$ is hydrogen; $R_2$ is halogen; $R_3$ is hydrogen; $R_4$, and $R_4'$ are selected from hydrogen; $R_5$ is selected from 6-8-membered heterocyclic rings; $R_6$ is selected from hydrogen, and halogens; and n is 0, 1, or 2.

In at least one embodiment, the compounds of Formula (I) are chosen from compounds wherein X is C(R'); R' is selected from hydrogen; R is hydrogen; $R_1$ is chosen from hydrogen, and C1-C3 linear alkyl groups optionally substituted with one to three Rx; Rx is selected from halogens, and —OH; $R_2$ is halogen; $R_3$ is hydrogen; $R_4$, and $R_4'$ are selected from hydrogen; $R_5$ is selected from 6-8-membered heterocyclic rings; $R_6$ is selected from hydrogen, and halogens; and n is 0, 1, or 2.

In at least one embodiment, the compounds of Formula (I) are chosen from compounds wherein X is N; R is hydrogen; $R_1$ is chosen from hydrogen, and C1-C3 linear alkyl groups optionally substituted with one to three Rx; Rx is selected from halogens, and —OH; $R_2$ is hydrogen; $R_3$ is hydrogen; $R_4$, and $R_4'$ are selected from hydrogen and $CH_3$; $R_5$ is selected from 6-8-membered heterocyclic rings; $R_6$ is selected from hydrogen, and halogens; and n is 0, 1, or 2.

Preferably, the compound is a compound of Formula (I) that is a USP28 Inhibitor, a USP25 Inhibitor and/or a USP 28/25 Inhibitor as defined herein.

As used herein, heterocycloalkyl is understood to mean monocyclic or polycyclic rings. The group can be fused (e.g., decalin) or bridged (e.g., norbornane). Moreover, there are not delocalized π electrons (aromaticity) shared among the entire ring carbons or heteroatoms.

Pharmaceutical forms of the compounds disclosed herein can include pharmaceutically acceptable salts, solvates, and the like. Unless indicated otherwise, all pharmaceutical forms, such as all tautomeric forms and stereoisomers, are contemplated herein as part of the present disclosure. Unless otherwise indicated with an asterisk (*), stereochemistry indicated herein refers to the relative (arbitrarily assigned) stereochemical orientation within each molecule, which is not necessarily the same as the absolute stereochemistry.

The compounds for inhibiting USP28 and/or USP25 provided herein are useful to inhibit USP28 and/or USP25, as well as in the development of pharmaceutical compositions for treatment of human disease or disease symptomology associated with activity of USP28 and/or USP25. A USP 28 Inhibitor disclosed herein can be used for the development of pharmaceutical compositions for the treatment of disease, such as cancer (e.g., lung cancer). A USP 25 Inhibitor disclosed herein can be used for the development of pharmaceutical compositions for the treatment of disease, such as cancer (e.g., lung cancer). A compound of Formula (I) can be both a USP 28 Inhibitor and a USP25 Inhibitor disclosed herein used for the development of pharmaceutical compositions for the treatment of disease, such as cancer (e.g., lung cancer).

A compound of Formula (I) that is a USP28 Inhibitor and/or a USP25 Inhibitor can be formulated in a pharmaceutical composition for administration to a subject (animal or human) or sample (e.g., comprising one or more cells containing USP 28 and/or USP25) in a therapeutically effective manner selected to elicit a desired and/or therapeutic biological or medicinal response or effect in a cell, tissue, system, animal, individual or human, including any one or more of the following: (1) preventing the disease (for example, preventing a disease, condition or disorder in an individual that may be predisposed to the disease, condition or disorder but does not yet experience or display the pathology or symptomatology of the disease), (2) inhibiting the progression of a disease (for example, slowing or arresting the progression of a disease or symptoms of a disease, condition or disorder in an individual that is experiencing or displaying the pathology or symptomatology of the disease, condition or disorder, including arresting further development of the pathology and/or symptomatology), or (3) ameliorating the disease or symptoms thereof (for example, reducing the frequency or intensity of a symptom associated with a disease, condition or disorder in an individual that is experiencing or displaying the pathology or symptomatology of the disease, condition or disorder including reversing the pathology and/or symptomatology). The USP28 and/or USP25 inhibitor compounds disclosed herein can be used in an amount effective to provide an intended effect.

While not being bound by any specific theory, Applicants believe that the compounds of Formula (I) and pharmaceutical forms thereof are useful for inhibition of USP28 and/or USP25. This inhibition can result in useful treatment of the symptoms and/or underlying causes of diseases or conditions where USP28 and/or USP25 needs inhibition. For example, inhibitors of USP28 and/or USP25 can be used to treat cancer, such as lung cancer.

Another aspect of the disclosure is directed to pharmaceutical compositions comprising a compound chosen from compounds of Formula (I), and pharmaceutical forms thereof, with a pharmaceutically acceptable carrier. The pharmaceutical acceptable carrier may further include an excipient, diluent, or surfactant. The compounds disclosed herein for USP28 and/or USP25 inhibition can be combined with pharmaceutically acceptable excipients suitable for an intended route of administration to a human or animal. The excipients can be selected to provide a pharmaceutical dosage form suitable for an intended route of administration, including oral or parenteral administration dosage forms.

Accordingly, the present disclosure relates to provided methods of treating a disease or disorder associated with USP28 and/or USP25 comprising administering to a patient suffering from at least one of said diseases or disorders a compound of Formula (I) and/or pharmaceutical forms thereof, optionally in a pharmaceutical composition. The disclosed compounds can be administered in effective amounts to treat or prevent a disorder and/or prevent the development thereof in subjects. Methods of treating a disease or disorder with a compound known to inhibit USP28 and/or USP25 with an IC50 of less than about 1 micromolar or less in the Ubiquitin-Rhodamine 110 Assays for USP28 and/or USP25 as described in Examples A-1(a), A-1(b), and A-2 herein can comprise administering to a patient in need thereof a therapeutically effective amount of a pharmaceutical composition comprising a compound of Formula (I). Preferably, the pharmaceutical composition comprises a USP28 and/or USP25 inhibitor compound of Formula (I) and/or a USP28 and/or USP25 inhibitor compound having an IC50 of less than about 1 micromolar or less in the Ubiquitin-Rhodamine 110 Assays for USP28 and/or USP25 as described in Examples A-1(a), A-1(b), and A-2 herein.

Non-limiting examples of compounds according to Formula (I) of the disclosure include those of Tables 1, 2, 3, and 4 below.

Methods of Synthesizing the Compounds

The compounds of the present disclosure can be prepared in a number of ways known to those skilled in the art of organic synthesis. The compounds of the present disclosure may be made by a variety of methods, including standard chemistry. Suitable synthetic routes are depicted in the Schemes provided herein. The compounds disclosed herein may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

The compounds described herein may be made from commercially available starting materials or synthesized using known organic, inorganic, and/or enzymatic processes. Those skilled in the art will recognize if a stereocenter exists in the compounds disclosed herein. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

By way of example, compounds of the present disclosure can be synthesized using the methods described below, together with synthetic methods known in the art of synthetic organic chemistry, or variations thereof as appreciated by those skilled in the art. General procedures to prepare compounds of the instant invention are described in General Scheme 1. An appropriately substituted and protected bicyclic intermediate 1 can be reacted with an appropriately substituted protected amine intermediate 2 under palladium-catalyzed carbon-nitrogen coupling protocols using an appropriate palladium complex, ligand, and base (such as but not limited to: RuPhos 3$^{rd}$ generation palladium precatalyst and cesium carbonate) in a suitable solvent such as toluene at an appropriate temperature (such as 100° C.) to afford intermediate 3. The protecting group 1 (PG$_1$; typically a Cbz group) can be removed under suitable deprotection conditions (such as but not limited to: hydrogen (gas), with palladium on carbon in an appropriate solvent such as methanol, ethanol, or ethyl acetate) to afford amine intermediate 4. The suitably substituted amine intermediate 4 can be reacted with a suitably substituted carboxylic acid under amide coupling conditions (such as but not limited to: the coupling reagents EDC and HOBt with an appropriate base such as Et$_3$N or DIEA in a solvent such as DMF or DMA) to afford the penultimate amide intermediate 5. The protecting group 2 (PG$_2$; typically a Boc group) can be removed under appropriate conditions such as TFA in a solvent such as DCM or HCl in a solvent such as MeOH or dioxane to afford the final compounds 6. The final compounds can be typically purified by preparative HPLC and isolated as the free base. In the case where mixtures of enantiomers and/or diastereomers are formed, the individual stereoisomers can be purified at an appropriate stage, in many cases by chiral HPLC.

salt 4 under palladium-catalyzed coupling conditions (such as Pd(dppf)Cl$_2$, RuPhos, Cs$_2$CO$_3$, in a solvent system such as toluene/water at elevated temperature) to afford the coupled product. The Cbz protecting group can be removed under hydrogenolysis conditions (such as under a hydrogen atmosphere with 10% Pd/C in a solvent such as EtOAc) to afford the amine 5. Amine 5 can be reacted with an appropriately substituted carboxylic acid 6 under amide coupling conditions (such as EDCI, HOBt with DIEA as the base in a solvent such as DCM) to afford an amide product that can be further deprotected under BOC-deprotection conditions (such as TFA/DCM) to afford product 7.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to

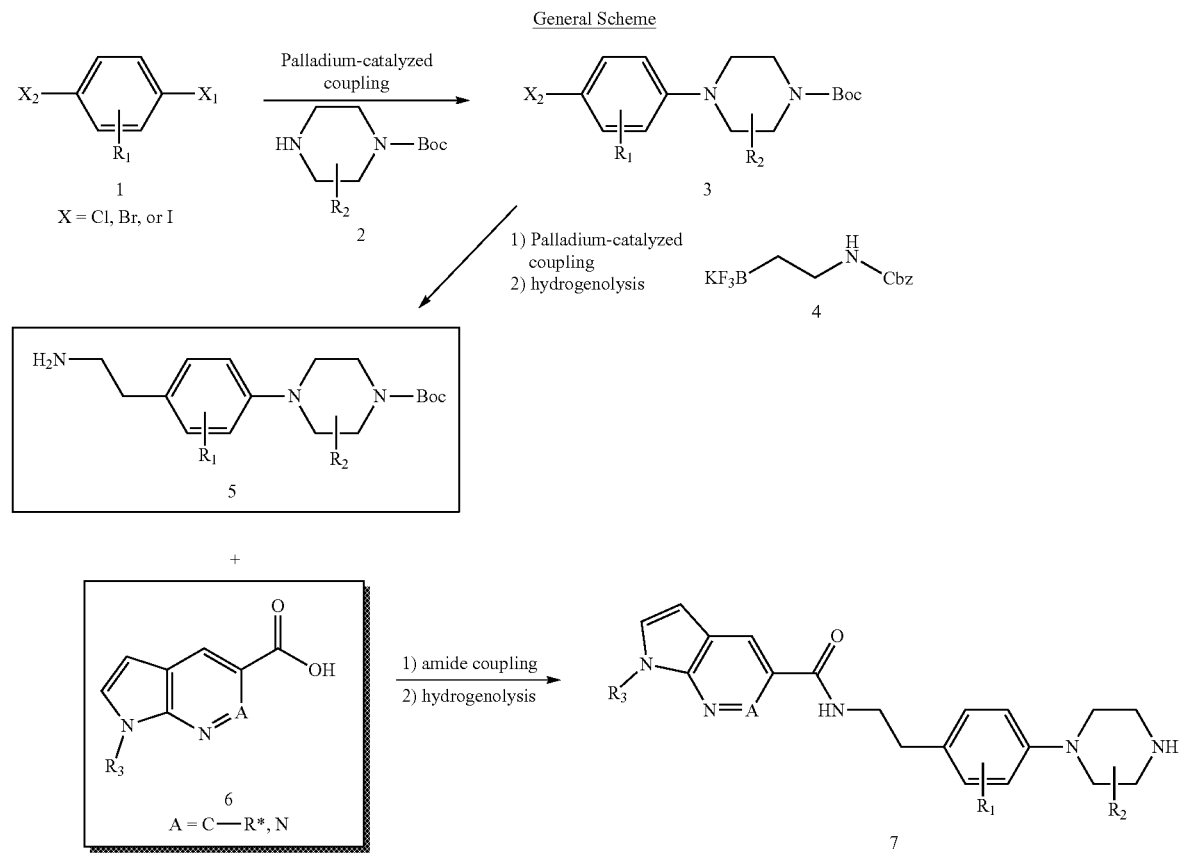

General Scheme

An appropriately substituted aryl halide 1 (containing two halogens selecting from Cl, Br, or I) is reacted with an appropriately substituted protected amine 2 under palladium-catalyzed carbon-nitrogen coupling conditions (such as Pd$_2$(dba)$_3$, XantPhos, sodium t-butoxide in a solvent such as toluene at elevated temperature) to afford the coupled aryl halide product 3. Aryl halide 3 is reacted with potassium BF$_3$ those skilled in the art without departing from the spirit of the present disclosure and/or scope of the appended claims.
Analytical Methods, Materials, and Instrumentation Unless otherwise noted, reagents and solvents were used as received from commercial suppliers. Unless otherwise noted, reactions were conducted under an inert atmosphere of nitrogen. Proton nuclear magnetic resonance (NMR)

spectra were obtained on either Bruker or Varian spectrometers at 300 or 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 µm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted as designated below. The absolute configuration of the separated enantiomers of the compounds in the examples described herein was occasionally determined. In all other cases the absolute configuration of the separated enantiomers was not determined and in those instances the configuration of the resolved materials were arbitrarily assigned as R or S in each case.

Example A-1(a)

Biochemical Assay: Ubiquitin-Rhodamine 110 Assay for USP28 Activity

The assay was performed in a final volume of 9 µL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 µM filtered, Sigma, G7516-25G), and 0.01% Triton X-100 (Sigma, T9284-10L). Nanoliter quantities of 10-point, 3-fold serial dilution in DMSO was pre-dispensed into 1536 assay plates (Corning, #3724BC) for a final test concentration of 25 µM to 1.3 nM, top to lowest dose, respectively. Enzyme USP28, construct His-tagged USP28-FL-mammalian, (protein expression and purification procedure described below). Concentration and incubation times were optimized for the maximal signal-to-background while maintaining initial velocity conditions at a fixed substrate concentration. The final concentration of the enzyme in the assay was 75 pM. Final substrate (Ub-Rh110; Ubiquitin-Rhodamine 110, UbiQ-126) concentration was 25 nM with [Ub-Rh110]<<Km. 3 µL of 2× enzyme was added to assay plates (pre-stamped with compound) preincubated with USP25 for 30 minutes and then 3 µL of 2×Ub-Rh110 was added to assay plates. Plates were incubated for 45 minutes at room temperature before addition of 3 µL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Procedure for the Protein Expression and Purification for Construct His-Tagged USP28-FL-Mammalian Expression of USP28 (1-1077)-TEV-6*His (pTT5 vector) was carried out in Expi293f cells (sequence derived from uniprot ID: Q96RU2-1). Cells were re-suspended in lysis buffer B 50 mM Bicine, pH 8.0, 20 mM NaCl, 5% glycerol, 0.1% CHAPS, 5 mM β-ME, 1 mM PMSF, 1 µg/ml Leupeptin, 1 µg/ml Pepstatin) and lysed by sonication. Insoluble material was removed by centrifugation and the supernatant was loaded onto a Ni-NTA column (GE Healthcare) equilibrated with Ni Buffer A (50 mM Bicine, pH 8.0, 20 mM NaCl, 5% glycerol, 0.1% CHAPS, 5 mM β-ME.) and washed with Ni Buffer A+20 mM imidazole until $A_{280}$ reached baseline. The protein was eluted with Ni Buffer B (50 mM Bicine, pH 8.0, 20 mM NaCl, 5% glycerol, 0.1% CHAPS, 5 mM β-ME, 300 mM imidazole.). The protein was further purified using a Superdex™ 200 10/300 GL column (GE Healthcare) equilibrated with 50 mM Bicine, pH 8.0, 20 mM NaCl, 5% glycerol, 0.1% CHAPS, 5 mM β-ME. The protein was concentrated to 2.5 mg ml$^{-1}$, flash-frozen in liquid $N_2$ and stored at −80° C.

Example A-1(b)

Biochemical Assay: Ubiquitin-Rhodamine 110 Assay for USP28 Activity

Each assay was performed in a final volume of 20 µL in assay buffer containing 20 mM Tris-HCl (pH 8.0, (1M Tris-HCl, pH 8.0 solution; Corning 46-031-CM)), 2 mM $CaCl_2$ (1M Calcium Chloride solution; Sigma #21114) 2 mM BME (2-Mercaptoethanol; Sigma 63689-25ML-F), 0.01% Prionex (0.22 µM filtered, Sigma #G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 µM ($DMSO_{(fc)}$=0.5%). Enzyme (USP28, construct USP28 (USP28-5(1-1077)-TEV-6*His; LifeSensors) concentration and incubation times were optimized for the maximal signal-to-background while maintaining initial velocity conditions at a fixed substrate concentration. The final concentration of the enzyme in the assay was 400 pM. Final substrate (Ub-Rh110; Ubiquitin-Rhodamine 110, R&D Systems #U-555) concentration was 25 nM with [Ub-Rh110]<<Km. 10 µL of 2× enzyme was added to assay plates (pre-stamped with compound) either simultaneously with 2×Ub-Rh110 or preincubated with USP28 40 minutes prior to the addition of 10 µL of 2×Ub-Rh110 to compound plates. Plates were incubated stacked for 90 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

For follow-up studies, each assay was performed in a final volume of 15 µL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 µM filtered, Sigma, G7516-25G), and 0.01% Triton X-100 (Sigma, T9284-10L). Nanoliter quantities of either an 8-point or 10-point, 3-fold serial dilution in DMSO was pre-dispensed into assay plates (Perkin Elmer, ProxiPlate-384 F Plus, #) for a final test concentration of either 25 µM to 11 nM or 25 µM to 1.3 nM, respectively. Enzyme USP28, construct USP28 (USP28-5 (1-1077)-TEV-6*His; LifeSensors) concentration and incubation times were optimized for the maximal signal-to-background while maintaining initial velocity conditions at a fixed substrate concentration. The final concentration of the enzyme in the assay was 75 pM. Final substrate (Ub-Rh110; Ubiquitin-Rhodamine 110, R&D Systems #U-555)

concentration was 25 nM with [Ub-Rh110]<<Km. 5 μL of 2× enzyme was added to assay plates (pre-stamped with compound) preincubated with USP28 for 30 minutes and then 5 μL of 2×Ub-Rh110 was added to assay plates. Plates were incubated stacked for 20 minutes at room temperature before 5 μL of stop solution was added (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example A-2

Biochemical Assay: Ubiquitin-Rhodamine 110 Assay for USP25 Activity

The assay was performed in a final volume of 9 μL in assay buffer containing 20 mM Tris-HCl (pH 8.0, (1M Tris-HCl, pH 8.0 solution; Corning 46-031-CM)), 3 mM BME (2-Mercaptoethanol; Sigma 63689-25ML-F), 0.03% BGG (0.22 μM filtered, Sigma, G7516-25G), and 0.01% Triton X-100 (Sigma, T9284-10L). Nanoliter quantities of 10-point, 3-fold serial dilution in DMSO was pre-dispensed into 1536 assay plates (Corning, #3724BC) for a final test concentration of 25 μM to 1.3 nM, top to lowest dose, respectively. Enzyme USP25, construct USP25-His6, (Boston Biochem E-546). Concentration and incubation times were optimized for the maximal signal-to-background while maintaining initial velocity conditions at a fixed substrate concentration. The final concentration of the enzyme in the assay was 75 pM. Final substrate (Ub-Rh110; Ubiquitin-Rhodamine 110, R&D Systems #U-555) concentration was 25 nM with [Ub-Rh110]<<Km. 3 μL of 2× enzyme was added to assay plates (pre-stamped with compound) preincubated with USP25 for 30 minutes and then 3 μL of 2×Ub-Rh110 was added to assay plates. Plates were incubated for 45 minutes at room temperature before addition of 3 μL of stop solution (final concentration of 10 mM citric acid (Sigma, 251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

For assay formats Examples A-1a, A-1b, and A-2, data were reported as percent inhibition compared with control wells based on the following equation: % inh=1−((FLU−$Ave_{Low}$)/($Ave_{High}$−$Ave_{Low}$)) where FLU=measured Fluorescence, $Ave_{Low}$=average Fluorescence of no enzyme control (n=16), and $Ave_{High}$=average Fluorescence of DMSO control (n=16). $IC_{50}$ values were determined by curve fitting of the standard 4 parameter logistic fitting algorithm included in the Activity Base software package: IDBS XE Designer Model205. Data is fitted using the Levenburg Marquardt algorithm.

The activity of compounds in the biochemical $IC_{50}$ assays ($IC_{50}$ ranges) according to the present disclosure are reported in Tables 1-4 below according to the following: "−": >10 μM; "+": 2-10 μM; "++": 0.2-2 μM; "+++": 0.05-0.2 μM; "++++": 0.001-0.05 μM.

Example 1-1

N-[2-(4-[3,8-diazabicyclo[3.2.1]octan-3-yl]-2,5-difluorophenyl)ethyl]-1-ethyl-1H-pyrrolo[2,3-b]pyridine-5-carboxamide

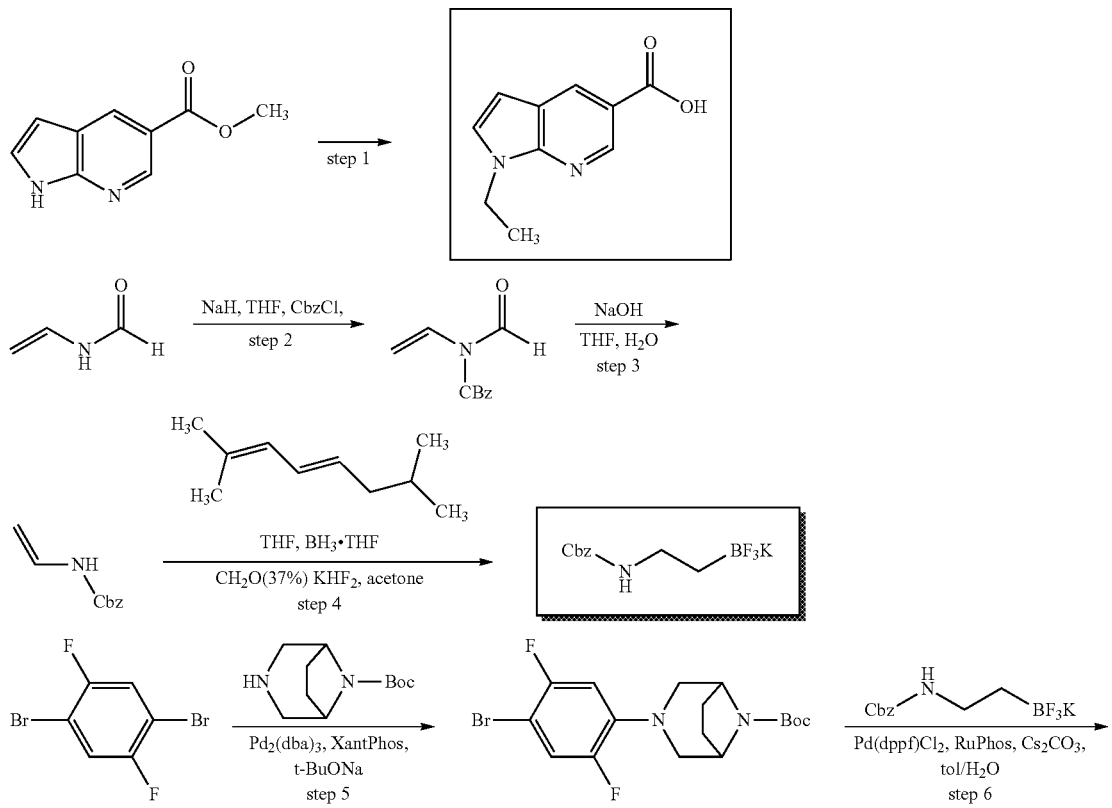

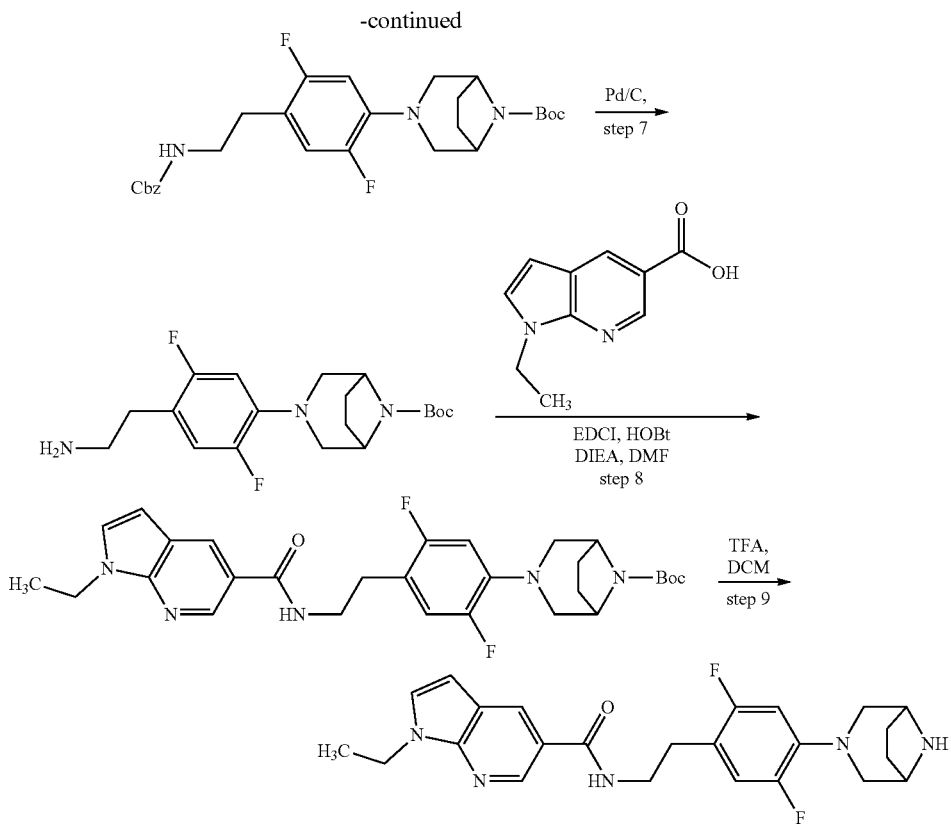

Step 1. 1-Ethyl-1H-pyrrolo[2,3-b]pyridine-5-carboxylic acid

To a stirred solution of methyl 1H-pyrrolo[2,3-b]pyridine-5-carboxylate (3.00 g, 17.0 mmol) in N,N-dimethylformamide (80 mL) at 0° C. was added sodium hydride (2.04 g, 51.1 mmol, 60% dispersion). The resulting solution was stirred for 1 h at 0° C. Iodoethane (2.73 mL, 34.1 mmol) was added at 0° C. The resulting solution was stirred for 10 h at room temperature (25° C.). The reaction was quenched with 10 mL of water. After stirring for 0.5 h the pH value of the solution was adjusted to 7-8 with hydrochloric acid (3N). The resulting mixture was extracted with ethyl acetate (6×50 mL). The organic layers were combined, washed with brine (50 mL), dried over anhydrous sodium sulfate, filtered and concentrated under vacuum to afford 1-ethyl-1H-pyrrolo[2,3-b]pyridine-5-carboxylic acid as a yellow solid that was carried on without further purification. LCMS: (ESI, m/z): 191 [M+H]$^+$

Step 2. Benzyl formyl(vinyl)carbamate

To a stirred solution of N-vinylformamide (100 g, 1.41 mol) in tetrahydrofuran (2 L) at 0° C. was added benzyl chloroformate (220 mL, 1.54 mol). The resulting solution was stirred for 30 min at 0° C. in an ice/salt bath. The resulting solution was allowed to stir for an additional 2 h while the temperature was maintained at 25° C., then was quenched by the addition of NH$_4$Cl (sat; 500 mL). The resulting mixture was extracted with ethyl acetate (4×500 mL). The organic layers were combined, dried over anhydrous sodium sulfate, filtered and concentrated under vacuum to afford benzyl formyl(vinyl)carbamate as light yellow oil. LCMS: (ESI, m/z): 206 [M+H]$^+$

Step 3. Benzyl Vinylcarbamate

A solution of sodium hydroxide (800 g, 20.0 mol) in water (1 L) was added into a stirred solution of benzyl formyl(vinyl)carbamate (166 g, 808 mmol) in tetrahydrofuran (1 L). The resulting solution was stirred for 3 h at 25° C., then the solvent was removed under vacuum. The resulting residue was extracted with ethyl acetate (3×500 mL). The organic layers were combined, dried over anhydrous sodium sulfate, filtered and concentrated under vacuum to afford a residue that was purified by a silica gel column chromatography (eluting with 1/10 ethyl acetate/petroleum ether) to afford benzyl vinylcarbamate as a light yellow solid. LCMS: (ESI, m/z): 178 [M+H]$^+$

Step 4. Benzyl (2-(trifluoro-λ4-boraneyl)ethyl)carbamate, Potassium Salt

To a solution of 2,5-dimethylhexa-2,4-diene (88.5 mL, 0.622 mol) in tetrahydrofuran (500 mL, 6.17 mol) under nitrogen was added a solution of BH$_3$ (313 mL, 1M in THF) at 0° C. The resulting solution was stirred for 3.5 h at 0° C. in a water/ice bath. Benzyl vinylcarbamate (20.0 g, 113 mmol) was then added into the mixture while maintaining the temperature at 0° C. The resulting solution was allowed to warm to 25° C., stirred for 2 h, cooled in an ice bath, then H$_2$O (35 mL) was carefully added. After an additional 2 h at 25° C., a solution of formaldehyde (15 mL, 37%) in water was added. The resulting mixture was then stirred overnight at 25° C. The reaction was quenched with brine, and the resulting mixture was extracted with ethyl acetate (3×500 mL). The organic layers were combined, dried over anhydrous sodium sulfate, filtered and concentrated under vacuum. To the residue was added acetone (500 mL), water (100 mL) and KHF$_2$ (220 g, 2.82 mol). The mixture was stirred at 25° C. for additional 4 h. The solvent was removed under vacuum. The residue was then extracted with hot acetone (500 mL). The insoluble salts were filtered off, and the filtrate was concentrated under vacuum. The crude compound was purified by dissolving in hot acetone and precipitating in Et$_2$O (350 mL) to afford benzyl (2-(trifluoro-λ4-boraneyl)ethyl)carbamate, potassium salt as a white solid. HRMS (ESI-, m/z): 212 [M−K$^+$]

Step 5. Tert-butyl 3-(4-bromo-2,5-difluorophenyl)-3,8-diazabicyclo[3.2.1]octane-8-carboxylate A mixture of 1,4-dibromo-2,5-difluorobenzene (15.0 g, 55.0 mmol), tert-butyl 3,8-diazabicyclo[3.2.1]octane-8-carboxylate (10.6 g, 49.9 mmol), Pd$_2$(dba)$_3$·CHCl$_3$ (2.59 g, 2.50 mmol), XantPhos (2.89 g, 5.00 mmol), and sodium tert-butoxide (9.60 g, 99.9 mmol) in toluene (500 mL) under nitrogen was stirred for 45 min at 70° C. After cooling to 25° C., the resulting mixture was concentrated under vacuum. The resulting residue was purified by silica gel column chromatography (eluting with 1:10 ethyl acetate/petroleum ether) to afford tert-butyl 3-(4-bromo-2,5-difluorophenyl)-3,8-diazabicyclo[3.2.1]octane-8-carboxylate as light yellow oil. LCMS: (ESI, m/z): 403, 405 [M+H]$^+$ Step 6. Tert-butyl 3-[4-(2-[[(benzyloxy)carbonyl] amino]ethyl)-2,5-difluorophenyl]-3,8-diazabicyclo [3.2.1]octane-8-carboxylate A mixture of tert-butyl 3-(4-bromo-2,5-difluorophenyl)-3,8-diazabicyclo[3.2.1]octane-8-carboxylate (14.0 g, 34.7 mmol), benzyl (2-(trifluoro-λ4-boraneyl)ethyl)carbamate, potassium salt (10.9 g, 38.2 mmol), Pd(dppf)Cl$_2$ (2.55 g, 3.49 mmol), RuPhos (3.25 g, 6.96 mmol), Cs$_2$CO$_3$ (22.7 g, 69.7 mmol), toluene (500 mL) and water (100 mL) under nitrogen was stirred for 3 h at 100° C. After cooling to 25° C., the resulting mixture was concentrated under vacuum. The resulting residue was purified by silica gel column chromatography (eluting with 1:5 ethyl acetate/petroleum ether) to afford tert-butyl 3-[4-(2-[[(benzyloxy)carbonyl] amino]ethyl)-2,5-difluorophenyl]-3,8-diazabicyclo[3.2.1] octane-8-carboxylate as a yellow oil. LCMS: (ESI, m/z): 502 [M+H]$^+$ Step 7. Tert-butyl 3-[4-(2-aminoethyl)-2,5-difluorophenyl]-3,8-diazabicyclo[3.2.1]octane-8-carboxylate A mixture of tert-butyl 3-[4-(2-[[(benzyloxy)carbonyl] amino]ethyl)-2,5-difluorophenyl]-3,8-diazabicyclo[3.2.1] octane-8-carboxylate (12.0 g, 23.9 mmol), palladium on carbon (12.0 g, 10%), and ethyl acetate (500 mL) was stirred for 1 h at 20° C. under hydrogen atmosphere (balloon). The hydrogen atmosphere was purged by nitrogen, and the solids were removed by filtration over Celite. The filtrate was concentrated under vacuum to afford a residue that was purified by silica gel column chromatography (eluting with 10:1 dichloromethane/methanol) to afford tert-butyl 3-[4-(2-aminoethyl)-2,5-difluorophenyl]-3,8-diazabicyclo[3.2.1]octane-8-carboxylate as a light yellow oil. LCMS: (ESI, m/z): 368 [M+H]$^+$ Step 8. Tert-butyl 3-[4-[2-([1-ethyl-1H-pyrrolo[2,3-b]pyridin-5-yl]formamido)ethyl]-2,5-difluorophenyl]-3,8-diazabicyclo[3.2.1]octane-8-carboxylate A solution of 1-ethyl-1H-pyrrolo[2,3-b]pyridine-5-carboxylic acid (60 mg, 0.32 mmol), tert-butyl 3-[4-(2-aminoethyl)-2,5-difluorophenyl]-3,8-diazabicyclo[3.2.1]octane-8-carboxylate (116 mg, 0.320 mmol), HOBt (51 mg, 0.38 mmol), EDCI (86 mg, 0.450 mmol) and DIEA (0.100 mL, 0.630 mmol) in dichloromethane (8 mL) was stirred for 2 h at 40° C. in an oil bath. The resulting mixture was concentrated under vacuum to afford a residue that was purified by a silica gel column chromatography (eluting with 1/1 ethyl acetate/petroleum ether). The collected fractions were combined and concentrated under vacuum to afford tert-butyl 3-[4-[2-([1-ethyl-1H-pyrrolo[2,3-b]pyridin-5-yl]formamido)ethyl]-2,5-difluorophenyl]-3,8-diazabicyclo[3.2.1]octane-8-carboxylate as a white solid. LCMS (ESI, m/z): 540 [M+H]$^+$.

Step 9. N-[2-(4-[3,8-diazabicyclo[3.2.1]octan-3-yl]-2,5-difluorophenyl)ethyl]-1-ethyl-1H-pyrrolo[2,3-b] pyridine-5-carboxamide A solution of tert-butyl 3-[4-[2-([1-ethyl-1H-pyrrolo[2,3-b]pyridin-5-yl]formamido)ethyl]-2,5-difluorophenyl]-3,8-diazabicyclo[3.2.1]octane-8-carboxylate (50 mg, 0.090 mmol) and trifluoroacetic acid (1 mL) in dichloromethane (5 mL) was stirred for 30 min at 25° C. The resulting mixture was concentrated under vacuum to afford a residue that was treated with a solution of NH$_3$ (2 mL, 7M in MeOH). The resulting solution was stirred for 0.5 h, and then concentrated under vacuum to afford a residue that was purified by Prep-HPLC (Column: XBridge BEH C18 OBD Prep Column, 130 Å, 5 µm, 19 mm×150 mm; Mobile phase, A: water (containing 10 mmol NH$_4$HCO$_3$) and B: MeCN (18% up to 38% over 7 min); Flow rate: 30 mL/min; Detector: 254 & 220 nm) to afford N-[2-(4-[3,8-diazabicyclo[3.2.1]octan-3-yl]-2,5-difluorophenyl)ethyl]-1-ethyl-1H-pyrrolo[2,3-b] pyridine-5-carboxamide as a white solid.

$^1$H-NMR (CD$_3$OD, 400 MHz) δ (ppm): 8.66 (s, 1H), 8.36 (s, 1H), 7.52 (d, J=3.6 Hz, 1H), 7.01-6.96 (m, 1H), 6.66 (dd, J=11.6, 7.6 Hz, 1H), 6.59 (d, J=3.6 Hz, 1H), 4.36 (q, J=7.2 Hz, 2H), 3.63-3.56 (m, 4H), 3.23-3.20 (m, 2H), 2.91-2.87 (m, 4H), 2.02-1.97 (m, 2H), 1.93-1.84 (m, 2H), 1.45 (t, J=7.2 Hz, 3H). LCMS (ES, m/z): 440 [M+H]$^+$ The compounds in Table 1 can be prepared using the methods described for Example 1-1

TABLE 1

| Ex. # | Structure and Compound Name | LRMS m/z [M + H]+ | 1H NMR | Assay A-1(a) | Assay A-1(b) | Assay A-2 |
|---|---|---|---|---|---|---|
| 1-1 | N-(4-(3,8-diazabicyclo[3.2.1]octan-3-yl)-2,5-difluorophenethyl)-1-ethyl-1H-pyrrolo[2,3-b]pyridine-5-carboxamide | 440 | See above | ++++ | +++ | +++ |
| 1-2 | N-(4-(piperazin-1-yl)phenethyl)-1H-pyrrolo[2,3-b]pyridine-5-carboxamide | 350 | | ++ | + | ++ |
| 1-3 | 1-methyl-N-(4-(piperazin-1-yl)phenethyl)-1H-pyrrolo[2,3-b]pyridine-5-carboxamide | 364 | (DMSO-$d_6$, 300 MHz) δ (ppm): 8.74 (s, 1H), 8.57 (br s, 1H), 8.41 (s, 1H), 7.61 (d, J = 3.6 Hz, 1H), 7.09 (d, J = 8.4 Hz, 2H), 6.85 (d, J = 8.7 Hz, 2H), 6.58 (d, J = 3.6 Hz, 1H), 3.85 (s, 3H), 3.47-3.42 (m, 2H), 3.00-2.96 (m, 4H), 2.83-2.74 (m, 6H), 2.27 (br s, 1H) | ++ | ++ | ++ |
| 1-4 | 1-ethyl-N-(4-(piperazin-1-yl)phenethyl)-1H-pyrrolo[2,3-b]pyridine-5-carboxamide | 378 | (DMSO-$d_6$, 300 MHz) δ (ppm): 8.73 (s, 1H), 8.56 (m, 1H), 8.41 (s, 1H), 7.68 (d, J = 3.3 Hz, 1H), 7.09 (d, J = 8.4 Hz, 2H), 6.85 (d, J = 8.4 Hz, 2H), 6.58 (d, J = 3.6 Hz, 1H), 4.32 (q, J = 7.2 Hz, 2H), 3.49-3.42 (m, 2H), 3.00-2.96 (m, 4H), 2.83-2.74 (m, 6H), 1.39 (t, J = 7.2 Hz, 3H) | ++++ | +++ | ++ |

TABLE 1-continued

| Ex. # | Structure and Compound Name | LRMS m/z [M + H]+ | 1H NMR | Assay A-1(a) | Assay A-1(b) | Assay A-2 |
|---|---|---|---|---|---|---|
| 1-5 | 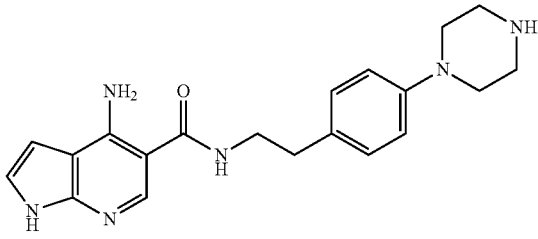<br>4-amino-N-(4-(piperazin-1-yl)phenethyl)-1H-pyrrolo[2,3-b]pyridine-5-carboxamide | 365 | (CD$_3$OD, 300 MHz) δ (ppm): 8.15 (s, 1H), 7.26-7.20 (m, 2H), 7.09 (d, J = 3.6 Hz, 1H), 6.99-6.94 (m, 2H), 6.62 (d, J = 3.3 Hz, 1H), 3.58-3.53 (m, 2H), 3.30-3.13 (m, 8H), 2.89-2.84 (m, 2H) | ++ | + | + |
| 1-6 | 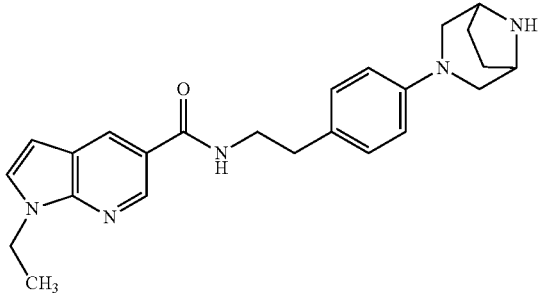<br>N-(4-(3,8-diazabicyclo[3.2.1]octan-3-yl)phenethyl)-1-ethyl-1H-pyrrolo[2,3-b]pyridine-5-carboxamide | 404 | (CD$_3$OD, 400 MHz) δ (ppm): 8.67 (s, 1H), 8.36 (s, 1H), 7.51 (d, J = 3.6 Hz, 1H), 7.13 (d, J = 8.4 Hz, 2H), 6.81 (d, J = 7.6 Hz, 2H), 6.58 (d, J = 3.6 Hz, 1H), 4.36 (q, J = 7.2 Hz, 2H), 3.69-3.67 (m, 2H), 3.59-3.56 (m, 2H), 3.47-3.44 (m, 2H), 2.88-2.82 (m, 4H), 1.91-1.86 (m, 4H), 1.45 (t, J = 7.2 Hz, 3H) | ++++ | ++++ | +++ |
| 1-7 | 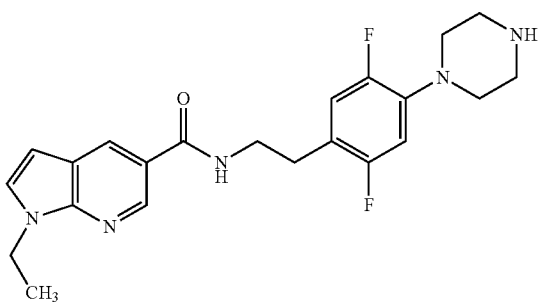<br>N-(2,5-difluoro-4-(piperazin-1-yl)phenethyl)-1-ethyl-1H-pyrrolo[2,3-b]pyridine-5-carboxamide | 414 | (CD$_3$OD, 400 MHz) δ (ppm): 8.66 (s, 1H), 8.36 (s, 1H), 7.52 (d, J = 3.6 Hz, 1H), 7.01 (dd, J = 12.8, 7.2 Hz, 1H), 6.76 (dd, J = 11.2, 7.2 Hz, 1H), 6.59 (d, J = 3.6 Hz, 1H), 4.36 (q, J = 7.2 Hz, 2H), 3.61 (t, J = 7.2 Hz, 2H), 3.02-2.99 (m, 8H), 2.91 (t, J = 7.2 Hz, 2H), 1.45 (t, J = 7.2 Hz, 3H) | ++++ | +++ | ++ |

TABLE 1-continued

| Ex. # | Structure and Compound Name | LRMS m/z [M + H]+ | ¹H NMR | Assay A-1(a) | Assay A-1(b) | Assay A-2 |
|---|---|---|---|---|---|---|
| 1-8 | 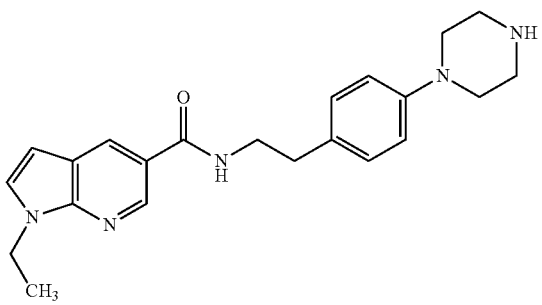<br>N-(4-(piperaizin-1-yl)phenethyl)-1-(2,2,2-trifluoroethyl)-1H-pyrrolo[2,3-b]pyridine-5-carboxamide | 432 | (CD$_3$OD, 300 MHz) δ (ppm): 8.77 (s, 1H), 8.41 (s, 1H), 7.57 (d, J = 8.3 Hz, 1H), 7.19 (d, J = 8.7 Hz, 2H), 6.95 (d, J = 8.7 Hz, 2H), 6.71 (d, J = 3.6 Hz, 1H), 5.14-5.08 (m, 2H), 3.61 (t, J = 7.2 Hz, 2H), 3.16-3.11 (m, 4H), 3.06-3.01 (m, 4H), 2.88 (t, J = 7.8 Hz, 2H) | ++++ | +++ | +++ |
| 1-9 | 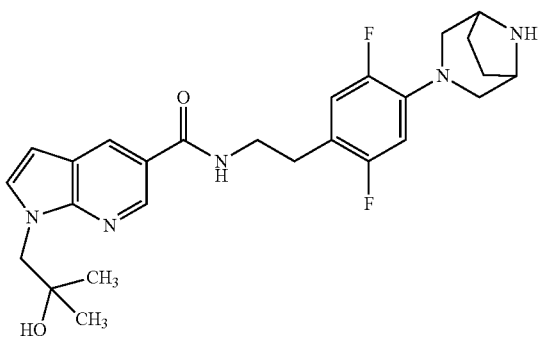<br>N-(4-(3,8-diazabicyclo[3.2.1]octan-3-yl)-2,5-difluorophenethyl)-1-(2-hydroxy-2-methylpropyl)-1H-pyrrolo[2,3-b]pyridine-5-carboxamide | 484 | (CD$_3$OD, 400 MHz) δ (ppm): 8.66 (s, 1H), 8.36 (s, 1H), 7.56 (d, J = 3.6 Hz, 1H), 6.98 (dd, J = 13.2, 7.2 Hz, 1H), 6.65 (dd, J = 11.2, 7.2 Hz, 2H), 6.59 (d, J = 3.6 Hz, 1H), 4.30 (s, 2H), 3.61-3.53 (m, 4H), 3.22-3.19 (m, 2H), 2.91-2.87 (m, 4H), 2.03-1.96 (m, 2H), 1.84-1.81 (m, 2H), 1.16 (s, 6H) | + | − | − |
| 1-10 | 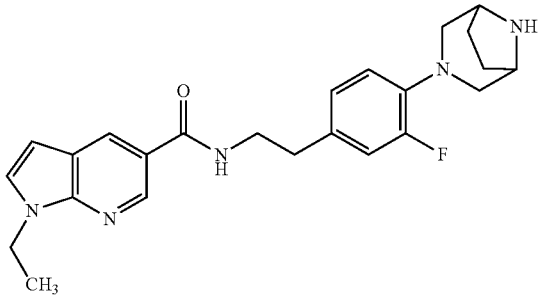<br>N-(4-(3,8-diazabicyclo[3.2.1]octan-3-yl)-3-fluorophenethyl)-1-ethyl-1H-pyrrolo[2,3-b]pyridine-5-carboxamide | 422 | (CD$_3$OD, 400 MHz) δ (ppm): 8.67 (s, 1H), 8.36 (s, 1H), 7.52 (d, J = 3.6 Hz, 1H), 7.00-6.95 (m, 2H), 6.90-6.85 (m, 1H), 6.59 (d, J = 3.2 Hz, 1H), 4.36 (q, J = 7.2 Hz, 2H), 3.61-3.54 (m, 4H), 3.19-3.13 (m, 2H), 2.93-2.85 (m, 4H), 2.02-2.01 (m, 2H), 1.90-1.80 (m, 2H), 1.48 (t, J = 7.2 Hz, 3H) | ++++ | +++ | ++ |

Example 2-1 and 2-2
N-[(2S)-2-[2,5-difluoro-4-(piperazin-1-yl)phenyl]propyl]-1-ethyl-1H-pyrrolo[2,3-b]pyridine-5-carboxamide and N-[(2R)-2-[2,5-difluoro-4-(piperazin-1-yl)phenyl]propyl]-1-ethyl-1H-pyrrolo[2,3-b]pyridine-5-carboxamide
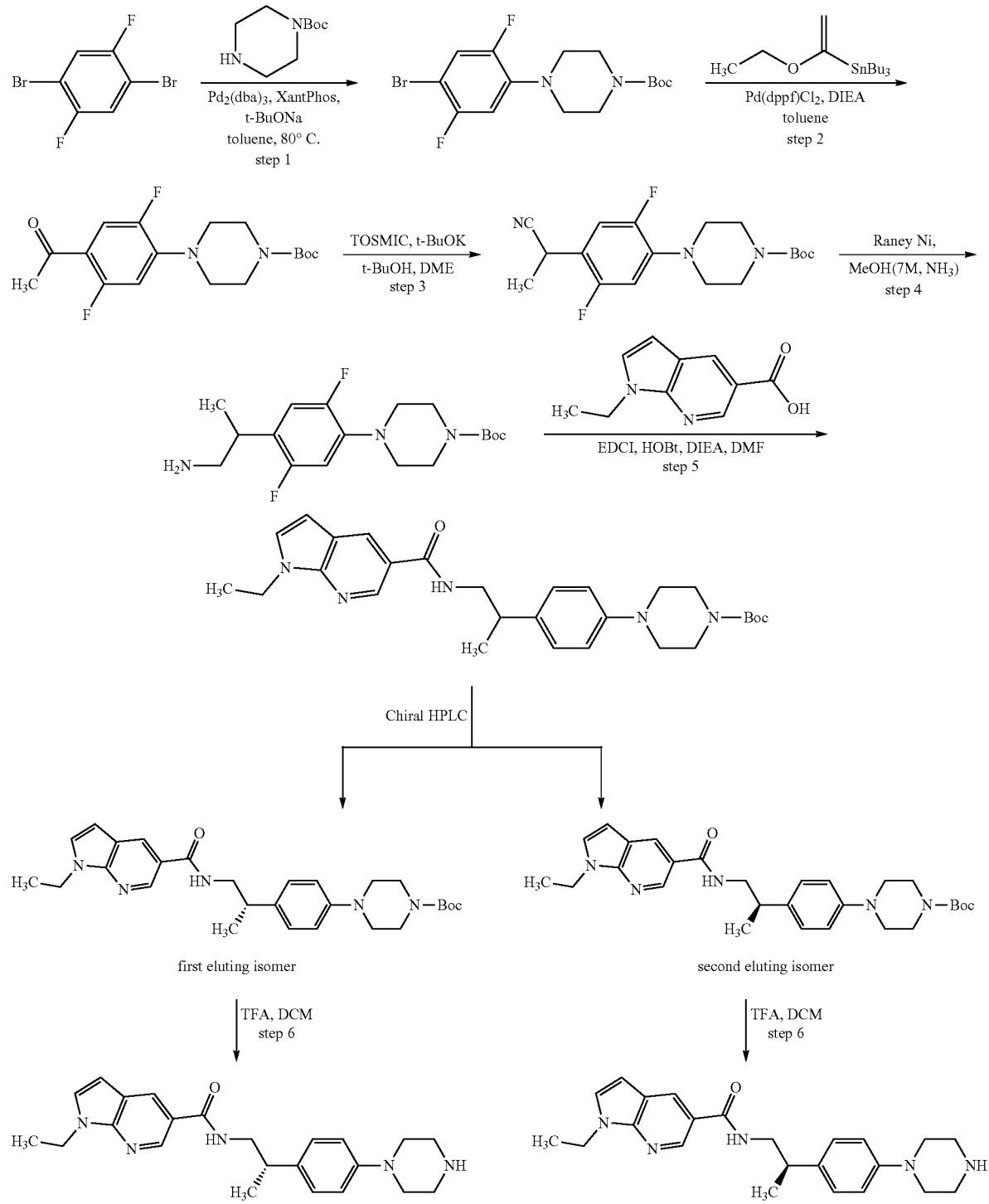

Step 1. tert-Butyl 4-(4-bromo-2,5-difluorophenyl) piperazine-1-carboxylate

A mixture of 1,4-dibromo-2,5-difluorobenzene (2.97 g, 10.9 mmol), tert-butyl piperazine-1-carboxylate (1.86 g, 9.99 mmol), Pd$_2$(dba)$_3$·CHCl$_3$ (0.518 g, 0.500 mmol), XantPhos (0.579 g, 1.00 mmol), and t-BuONa (1.92 g, 20.0 mmol) in toluene (100 mL) was stirred under nitrogen for 1 h at 70° C. After cooling to room temperature (25° C.), the resulting mixture was diluted with H$_2$O (50 mL), then was extracted with ethyl acetate (3×40 mL). The organic layers were combined, dried over anhydrous sodium sulfate, filtered and concentrated under vacuum to a residue that was purified by a silica gel column chromatography (eluting with 1/100-1/6 ethyl acetate/petroleum ether) to afford tert-butyl 4-(4-bromo-2,5-difluorophenyl)piperazine-1-carboxylate as a light yellow solid. LCMS (ESI, m/z):377 [M+H]$^+$.

Step 2. tert-Butyl 4-(4-acetyl-2,5-difluorophenyl) piperazine-1-carboxylate

A solution of tert-butyl 4-(4-bromo-2,5-difluorophenyl) piperazine-1-carboxylate (2.30 g, 6.10 mmol), Pd(dppf)Cl$_2$ (1.23 g, 1.68 mmol), DIEA (3.71 mL, 22.4 mmol), and tributyl(1-ethoxyethenyl)stannane (1.23 g, 3.41 mmol) in toluene (100 mL) was stirred under nitrogen for 18 h at 80° C. After cooling to room temperature (25° C.), the resulting mixture was diluted with H$_2$O (50 mL) and was extracted with ethyl acetate (3×40 mL). The organic layers were combined, dried over anhydrous sodium sulfate, filtered and concentrated under vacuum to a residue that was purified by a silica gel column chromatography (eluting with 1/100-1/2 ethyl acetate/petroleum ether) to afford tert-butyl 4-(4-acetyl-2,5-difluorophenyl)piperazine-1-carboxylate as a yellow solid. LCMS (ESI, m/z):341 [M+H]$^+$.

Step 3. Tert-butyl 4-[4-(1-cyanoethyl)-2,5-difluorophenyl]piperazine-1-carboxylate A solution of tert-butyl 4-(4-acetyl-2,5-difluorophenyl) piperazine-1-carboxylate (1.70 g, 4.99 mmol), t-BuOK (1.40 g, 12.5 mmol) and TOSMIC (1.46 g, 7.49 mmol) in tert-Butanol (20 mL) and ethylene glycol dimethyl ether (20 mL) was stirred for 18 h at 90° C. After cooling to room temperature (25° C.), the resulting mixture was diluted with H$_2$O (10 mL), then was extracted with ethyl acetate (3×20 mL). The organic layers were combined, dried over anhydrous sodium sulfate, filtered and concentrated under vacuum to a residue that was purified by a silica gel column chromatography (eluting with 1/100-1/5 ethyl acetate/petroleum ether) to afford tert-butyl 4-[4-(1-cyanoethyl)-2,5-difluorophenyl]piperazine-1-carboxylate as yellow oil. LCMS (ESI, m/z):352 [M+H]$^+$.

Step 4. tert-Butyl 4-[4-(1-aminopropan-2-yl)-2,5-difluorophenyl]piperazine-1-carboxylate A solution of NH$_3$ (7 M) in methanol (20 mL) was added into a stirring solution of tert-butyl 4-[4-(1-cyanoethyl)-2,5-difluorophenyl]piperazine-1-carboxylate (800 mg, 2.28 mmol) in methanol (20 mL). This solution was placed under nitrogen, and to this was added Raney Ni (wet) (800 mg). The resulting mixture was stirred for 2 h at 25° C. under a hydrogen atmosphere (balloon). The solids were removed by filtration over Celite, and the filtrate was concentrated under vacuum to a residue that was purified by a silica gel column chromatography (eluting with 10/1 dichloromethane/methanol) to afford tert-butyl 4-[4-(1-aminopropan-2-yl)-2,5-difluorophenyl]piperazine-1-carboxylate as yellow oil. LCMS (ESI, m/z): 356 [M+H]$^+$.

Step 5. tert-Butyl (S)-4-(4-(1-(1-ethyl-1H-pyrrolo[2,3-b]pyridine-5-carboxamido)propan-2-yl)-2,5-difluorophenyl)piperazine-1-carboxylate and tert-Butyl (R)-4-(4-(1-(1-ethyl-1H-pyrrolo[2,3-b]pyridine-5-carboxamido)propan-2-yl)-2,5-difluorophenyl)piperazine-1-carboxylate A solution of tert-butyl 4-[4-(1-aminopropan-2-yl)-2,5-difluorophenyl]piperazine-1-carboxylate (0.150 g, 0.420 mmol), 1-ethyl-1H-pyrrolo[2,3-b]pyridine-5-carboxylic acid (synthesis described above; 0.080 g, 0.420 mmol), EDCI (0.097 g, 0.510 mmol), HOBt (0.068 g, 0.500 mmol), and DIEA (0.210 mL, 1.26 mMol) in N,N-dimethylformamide (5 mL) was stirred for 18 h at 25° C. The resulting mixture was diluted with H$_2$O (10 mL), then was extracted with ethyl acetate (3×20 mL). The organic layers were combined, dried over anhydrous sodium sulfate, filtered and concentrated under vacuum to a residue that was purified by silica gel column chromatography (eluting with 1/1 ethyl acetate/petroleum ether) to afford a racemic mixture of tert-butyl 4-(4-(1-(1-ethyl-1H-pyrrolo[2,3-b]pyridine-5-carboxamido)propan-2-yl)-2,5-difluorophenyl)piperazine-1-carboxylate. The racemic product was separated into its individual enantiomers by Chiral-Prep-HPLC (Column, CHIRAL ART Cellulose-SB, 2×25 cm, 5 um; Mobile Phase, A: Hex and B: EtOH (hold 30% in 30 min); Flow rate: 20 mL/min; Detector: 220/254 nm; RT1: 10.28 min; RT2: 12.26 min). The fractions with the first eluting isomer (RT1:10.28 min) were collected and concentrated under vacuum to afford tert-butyl (S)-4-(4-(1-(1-ethyl-1H-pyrrolo[2,3-b]pyridine-5-carboxamido)propan-2-yl)-2,5-difluorophenyl)piperazine-1-carboxylate as white oil. The second eluting isomer fractions (RT1:12.26 min) were collected and concentrated under vacuum to afford tert-butyl (R)-4-(4-(1-(1-ethyl-1H-pyrrolo[2,3-b]pyridine-5-carboxamido)propan-2-yl)-2,5-difluorophenyl)piperazine-1-carboxylate as a white oil. LCMS (ESI, m/z): 528 [M+H]$^+$.

Step 6. N-[(2S)-2-[2,5-difluoro-4-(piperazin-1-yl) phenyl]propyl]-1-ethyl-M-pyrrolo[2,3-b]pyridine-5-carboxamide A solution of tert-butyl (S)-4-(4-(1-(1-ethyl-1H-pyrrolo [2,3-b]pyridine-5-carboxamido)propan-2-yl)-2,5-difluorophenyl)piperazine-1-carboxylate (0.050 g, 0.090 mmol) and trifluoroacetic acid (1 mL) in dichloromethane (4 mL) was stirred for 30 min at 25° C. The resulting mixture was concentrated under vacuum to a residue that was taken up into DCM (5 mL). The pH value was adjusted to 8 with a solution of NH$_3$ (7 M) in MeOH, and the resulting mixture was concentrated under vacuum to a residue that was purified by Prep-HPLC (Column: XBridge BEH C18 OBD Prep Column, 130 Å, 5 µm, 19 mm×150 mm; Mobile phase, A: water (containing 10 mmol NH$_4$HCO$_3$) and B: MeCN (30% up to 47% over 7 min); Flow rate: 20 mL/min; Detector: 254 & 220 nm) to afford N-[(2S)-2-[2,5-difluoro-4-(piperazin-1-yl)phenyl]propyl]-1-ethyl-1H-pyrrolo[2,3-b] pyridine-5-carboxamide as a yellow solid.
$^1$H-NMR (CDCl$_3$, 400 MHz) δ (ppm): 8.60 (s, 1H), 8.26 (s, 1H), 7.29 (d, J=3.6 Hz, 1H), 6.93 (dd, J=12.8, 6.8 Hz, 1H), 6.63 (dd, J=11.6, 7.6 Hz, 1H), 6.52 (d, J=3.6 Hz, 1H), 6.07 (br s, 1H), 4.38-4.33 (m, 2H), 3.84-3.77 (m, 1H), 3.54-3.47 (m, 1H), 3.40-3.34 (m, 1H), 3.07-3.05 (m, 8H), 1.48 (d, J=7.2 Hz, 3H), 1.32 (d, J=6.8 Hz, 3H). LCMS (ESI, m/z):428 [M+H]$^+$.

Step 7. N-[(2R)-2-[2,5-difluoro-4-(piperazin-1-yl)phenyl]propyl]-1-ethyl-1H-pyrrolo[2,3-b]pyridine-5-carboxamide A solution of tert-butyl (R)-4-(4-(1-(1-ethyl-1H-pyrrolo[2,3-b]pyridine-5-carboxamido)propan-2-yl)-2,5-difluorophenyl)piperazine-1-carboxylate (0.050 g, 0.090 mmol) and trifluoroacetic acid (1 mL) in dichloromethane (4 mL) was stirred for 30 minutes at 25° C. The resulting mixture was concentrated under vacuum to a solution that was diluted with DCM (5 mL). The pH value of the solution was adjusted to 8 with a solution of NH$_3$ (7 M) in MeOH. The resulting mixture was concentrated under vacuum to a residue that was purified by Prep-HPLC (Column: XBridge BEH C18 OBD Prep Column, 130 Å, 5 μm, 19 mm×150 mm; Mobile phase, A: water (containing 10 mmol NH$_4$HCO$_3$) and B: MeCN (30% up to 47% over 7 min); Flow rate: 20 mL/min; Detector: 254 & 220 nm) to afford N-[(2R)-2-[2,5-difluoro-4-(piperazin-1-yl)phenyl]propyl]-1-ethyl-1H-pyrrolo[2,3-b]pyridine-5-carboxamide as a yellow solid.

$^1$H-NMR (CD$_3$OD, 400 MHz) δ (ppm): 8.60 (s, 1H), 8.31 (s, 1H), 7.51 (d, J=3.6 Hz, 1H), 6.93 (dd, J=13.2, 6.8 Hz, 1H), 6.74 (dd, J=12.0, 7.2 Hz, 1H), 6.57 (d, J=3.6 Hz, 1H), 4.35 (q, J=7.2 Hz, 2H), 3.63-3.60 (m, 1H), 3.58-3.43 (m, 2H), 3.04-3.02 (m, 8H), 1.44 (d, J=7.2 Hz, 3H), 1.30 (d, J=8.0 Hz, 3H). LCMS (ESI, m/z): 428 [M+H]$^+$.

The compounds in Table 2 can be prepared using the methods described for Examples 2-1 and 2-2.

TABLE 2

| Ex. # | Structure and Compound Name | LRMS m/z [M + H]$^+$ | $^1$H NMR | Assay A-1(a) | Assay A-1(b) | Assay A-2 |
|---|---|---|---|---|---|---|
| 2-1 | 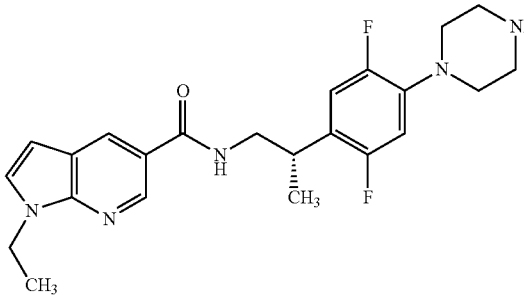<br>(S)-N-(2-(2,5-difluoro-4-(piperazin-1-yl)phenyl)propyl)-1-ethyl-1H-pyrrolo[2,3-b]pyridine-5-carboxamide | 428 | see above | +++ | ++ | ++ |
| 2-2 | 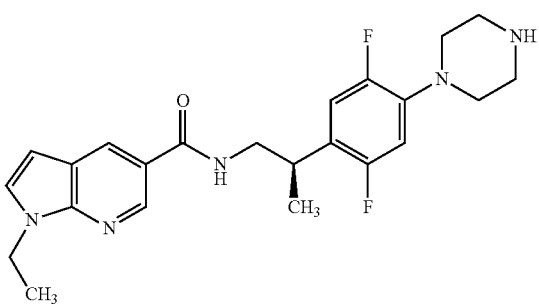<br>(R)-N-(2-(2,5-difluoro-4-(piperazin-1-yl)phenyl)propyl)-1-ethyl-1H-pyrrolo[2,3-b]pyridine-5-carboxamide | 428 | see above | ++ | + | + |

TABLE 2-continued

| Ex. # | Structure and Compound Name | LRMS m/z [M + H]+ | 1H NMR | Assay A-1(a) | Assay A-1(b) | Assay A-2 |
|---|---|---|---|---|---|---|
| 2-3 | N-((2R)-2-(4-(3,8-diazabicyclo[3.2.1]octan-3-yl)-2,5-difluorophenyl)propyl)-1-ethyl-1H-pyrrolo[2,3-b]pyridine-5-carboxamide | 454 | (CD$_3$OD, 400 MHz) δ (ppm): 8.61 (s, 1H), 8.31 (s, 1H), 7.51 (d, J = 3.6 Hz, 1H), 7.03 (q, J = 6.8 Hz, 1H), 6.64 (dd, J = 11.6, 7.2 Hz, 1H), 6.57 (d, J = 3.6 Hz, 1H), 4.36 (q, J = 6.8 Hz, 2H), 3.62-3.39 (m, 5H), 3.24-3.19 (m, 2H), 2.94-2.87 (m, 2H), 2.02-1.98 (m, 2H), 1.88-1.86 (m, 2H), 1.42 (t, J = 7.2 Hz, 3H), 1.38 (t, J = 7.2 Hz, 3H) | ++++ | ++ | ++ |
| 2-4 | N-((2S)-2-(4-(3,8-diazabicyclo[3.2.1]octan-3-yl)-2,5-difluorophenyl)propyl)-1-ethyl-1H-pyrrolo[2,3-b]pyridine-5-carboxamide | 454 | (CD$_3$OD, 400 MHz) δ (ppm): 8.61 (s, 1H), 8.31 (s, 1H), 7.51 (d, J = 3.6 Hz, 1H), 7.03 (q, J = 6.8 Hz, 1H), 6.64 (dd, J = 12.0, 7.6 Hz, 1H), 6.58 (d, J = 3.6 Hz, 1H), 4.35 (q, J = 7.2 Hz, 2H), 3.62-3.39 (m, 5H), 3.24-3.19 (m, 2H), 2.94-2.87 (m, 2H), 2.02-1.98 (m, 2H), 1.88-1.86 (m, 2H), 1.44 (t, J = 7.2 Hz, 3H), 1.29 (t, J = 6.8 Hz, 3H) | +++ | ++ | ++ |

Example 3-1

3-Chloro-1-ethyl-N-[2-[4-(piperazin-1-yl)phenyl]ethyl]-1H-pyrrolo[2,3-b]pyridine-5-carboxamide

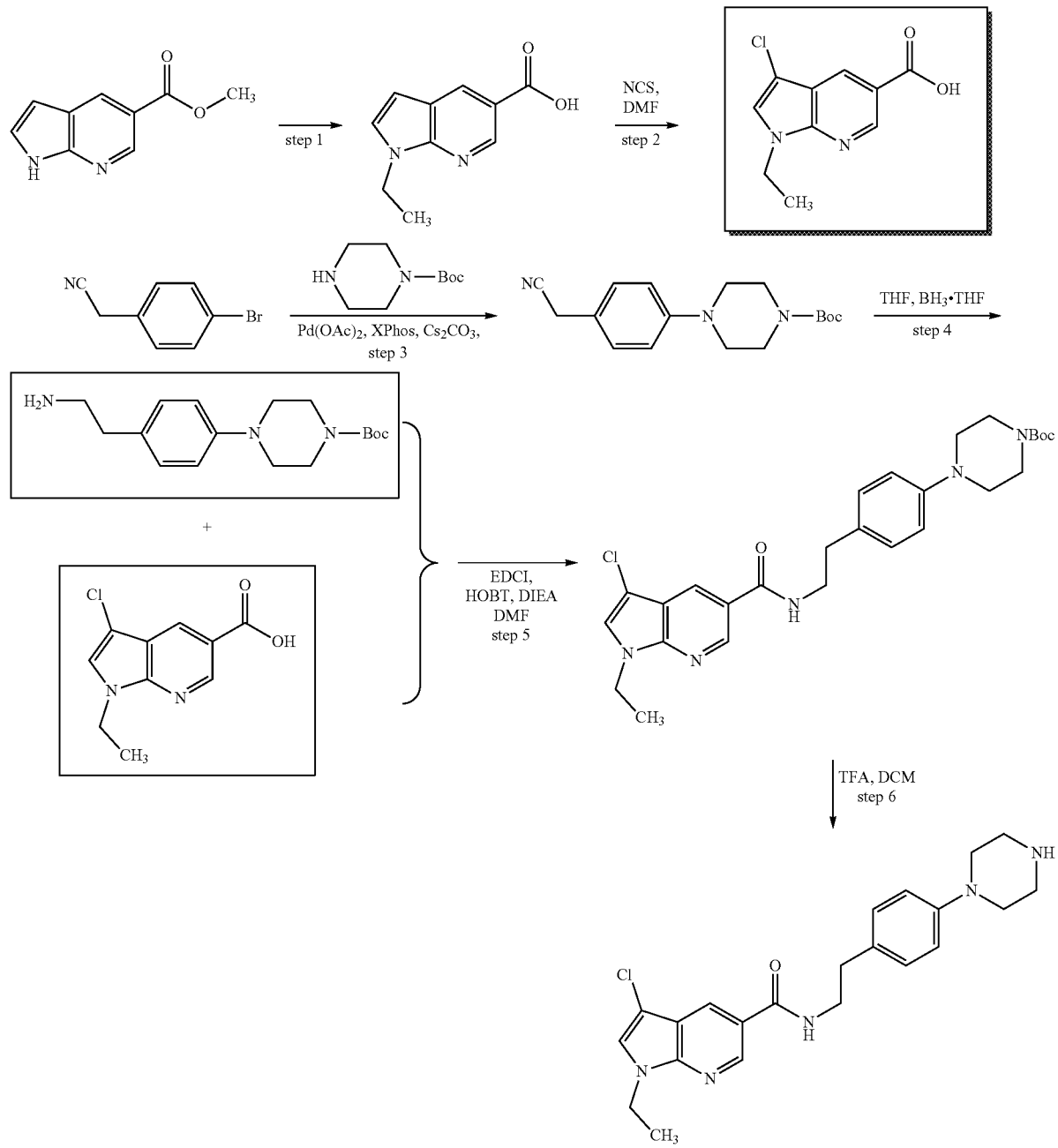

Step 1. 1-Ethyl-1H-pyrrolo[2,3-b]pyridine-5-carboxylic acid

To a stirred solution of methyl 1H-pyrrolo[2,3-b]pyridine-5-carboxylate (3.00 g, 17.0 mmol) in N,N-dimethylformamide (80 mL) at 0° C. was added sodium hydride (2.04 g, 51.1 mmol, 60% dispersion). The resulting solution was stirred for 1 h at 0° C. Iodoethane (2.73 mL, 34.1 mmol) was then added at 0° C. and the resulting solution was stirred for 10 h at room temperature (25° C.). The reaction was quenched carefully with water (10 mL). After stirring for 0.5 h, the pH value of the solution was adjusted to 7-8 with hydrochloric acid (3N). The resulting mixture was extracted with ethyl acetate (6×50 mL). The organic layers were combined, washed with brine (50 mL), dried over anhydrous sodium sulfate, filtered and concentrated under vacuum to afford 1-ethyl-1H-pyrrolo[2,3-b]pyridine-5-carboxylic acid as a yellow solid. LCMS: (ESI, m/z): 191 [M+H]$^+$

Step 2. 3-Chloro-1-ethyl-1H-pyrrolo[2,3-b]pyridine-5-carboxylic acid

A solution of 1-ethyl-1H-pyrrolo[2,3-b]pyridine-5-carboxylic acid (190 mg, 1.00 mmol) and NCS (147 mg, 1.10 mmol) in N,N-dimethylformamide (10 mL) was stirred for 18 h at 20° C. The resulting solution was diluted with 30 mL of H₂O, then was extracted with ethyl acetate (3×20 mL). The organic layers were combined, dried over anhydrous sodium sulfate, filtered and concentrated under vacuum to afford a residue that was purified by a silica gel column chromatography (eluting with 1/1 ethyl acetate/petroleum ether) to afford 3-chloro-1-ethyl-1H-pyrrolo[2,3-b]pyridine-5-carboxylic acid as a light yellow oil. LCMS (ESI, m/z): 225, 227 [M+H]⁺.

Step 3. tert-butyl 4-[4-(cyanomethyl)phenyl]piperazine-1-carboxylate 2-(4-bromophenyl)acetonitrile (5.00 g, 25.6 mmol), tert-butyl piperazine-1-carboxylate (7.16 g, 38.5 mmol), Pd(OAc)₂ (1.15 g, 5.13 mmol), XPhos (4.89 g, 10.0 mmol), Cs₂CO₃ (25.1 g, 76.9 mmol) and toluene (100 mL) were combined under a nitrogen atmosphere. The resulting solution was stirred 18 h at 100° C. After cooling to 20° C., the solids were removed by filtration and the resulting filtrate was concentrated under vacuum to afford a residue that was purified by a silica gel column chromatography (eluting with 1/2 ethyl acetate/petroleum ether) to afford tert-butyl 4-[4-(cyanomethyl)phenyl]piperazine-1-carboxylate as a yellow solid. LCMS (ESI, m/z): 302 [M+H]⁺.

Step 4. tert-butyl 4-[4-(2-aminoethyl)phenyl]piperazine-1-carboxylate

A solution of BH₃ (20 mL, 1M in THF) was added into a stirring solution of tert-butyl 4-[4-(cyanomethyl)phenyl]piperazine-1-carboxylate (1.80 g, 5.98 mmol) in THF (100 mL) under nitrogen. The resulting solution was stirred 2 h at 20° C., then was quenched by the addition of methanol. The resulting solution was stirred 2 h at 80° C. After cooling to 20° C., the reaction mixture was concentrated under vacuum to afford a residue that was purified by a silica gel column chromatography (eluting with 2/1 ethyl acetate/petroleum ether) to afford tert-butyl 4-[4-(2-aminoethyl)phenyl]piperazine-1-carboxylate as a black solid. LCMS (ESI, m/z): 306 [M+H]⁺.

Step 5. tert-butyl 4-(4-(2-(3-chloro-1-ethyl-1H-pyrrolo[2,3-b]pyridine-5-carboxamido)ethyl)phenyl)piperazine-1-carboxylate 3-chloro-1-ethyl-1H-pyrrolo[2,3-b]pyridine-5-carboxylic acid (100 mg, 0.444 mmol), tert-butyl 4-(4-(2-aminoethyl)phenyl)piperazine-1-carboxylate (163 mg, 0.530 mmol), EDCI (110 mg, 0.570 mmol), HOBt (73.0 mg, 0.540 mmol) and DIEA (0.150 mL, 0.890 mmol) were combined into N,N-dimethylformamide (5 mL) and stirred for 18 h at 20° C. The resulting solution was diluted with H₂O (50 mL), then was extracted with ethyl acetate (3×20 mL). The organic layers were combined, dried over anhydrous sodium sulfate, filtered and concentrated under vacuum to afford a residue that was purified by a silica gel column chromatography (eluting with 1/1 ethyl acetate/petroleum ether) to afford tert-butyl 4-(4-(2-(3-chloro-1-ethyl-1H-pyrrolo[2,3-b]pyridine-5-carboxamido)ethyl)phenyl)piperazine-1-carboxyl ate as a light yellow oil. LCMS (ESI, m/z): 512, 514 [M+H]⁺.

Step 6. 3-Chloro-1-ethyl-N-[2-[4-(piperazin-1-yl)phenyl]ethyl]-1H-pyrrolo[2,3-b]pyridine-5-carboxamide A solution of tert-butyl 4-(4-(2-(3-chloro-1-ethyl-1H-pyrrolo[2,3-b]pyridine-5-carboxamido)ethyl)phenyl)piperazine-1-carboxylate (80.0 mg, 0.156 mmol), and trifluoroacetic acid (1 mL) in dichloromethane (4 mL) was stirred for 30 min at 20° C. The resulting mixture was concentrated under vacuum to a residue that was purified by Prep-HPLC (Column Name: XBridge Prep C18 OBD Column, 150 mm*19 mm, 5 um; Mobile phase, A: Water (containing 10 mmol/L NH₄HCO₃) and B: MeCN (21% up to 46% over 8 min); Detector: UV 220&254 nm) to afford 3-chloro-1-ethyl-N-[2-[4-(piperazin-1-yl)phenyl]ethyl]-1H-pyrrolo[2,3-b]pyridine-5-carboxamide as a white solid.

¹H-NMR (CD₃OD, 300 MHz) δ (ppm): 8.77 (s, 1H), 8.38 (s, 1H), 7.62 (s, 1H), 7.19 (d, J=8.4 Hz, 2H), 6.96 (d, J=8.1 Hz, 2H), 4.37 (q, J=7.2 Hz, 2H), 3.62 (t, J=7.2 Hz, 2H), 3.13-3.11(m, 4H), 3.03-3.00 (m, 4H), 2.89 (t, J=7.2 Hz, 2H), 1.47 (t, J=7.2 Hz, 3H). LCMS (ESI, m/z): 412, 414 [M+H]⁺.

The compounds in Table 3 can be prepared using the methods described for Example 3-1.

TABLE 3

| Ex. # | Structure and Compound Name | LRMS m/z [M + H]⁺ | ¹H NMR | Assay A-1(a) | Assay A-1(b) | Assay A-2 |
| --- | --- | --- | --- | --- | --- | --- |
| 3-1 | 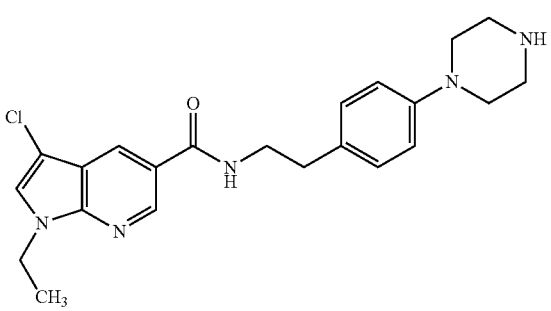3-chloro-1-ethyl-N-(4-(piperazin-1-yl)phenethyl)-1H-pyrrolo[2,3-b]pyridine-5-carboxamide | 412, 414 | see above | ++++ | +++ | +++ |

TABLE 3-continued
| Ex. # | Structure and Compound Name | LRMS m/z [M + H]+ | 1H NMR | Assay A-1(a) | Assay A-1(b) | Assay A-2 |
|---|---|---|---|---|---|---|
| 3-2 | 3-chloro-N-(4-(piperazin-1-yl)phenethyl)-1H-pyrrolo[2,3-b]pyridine-5-carboxamide | 384, 386 | (DMSO-d6, 400 MHz) δ (ppm): 1.22 (br s, 1H), 8.77 (s, 1H), 8.68 (br s, 1H), 8.38 (d, J = 2.0 Hz, 1H), 7.77 (s, 1H), 7.08 (d, J = 8.4 Hz, 2H), 6.83 (d, J = 8.4 Hz, 2H), 3.47-3.42 (m, 3H), 2.97-2.95 (m, 4H), 2.85-2.73 (m, 6H) | ++ | + | + |
Example 4-1
N-[2-(4-[3,8-diazabicyclo[3.2.1]octan-3-yl]-2,5-difluorophenyl)ethyl]-7-ethyl-7H-pyrrolo[2,3-c]pyridazine-3-carboxamide
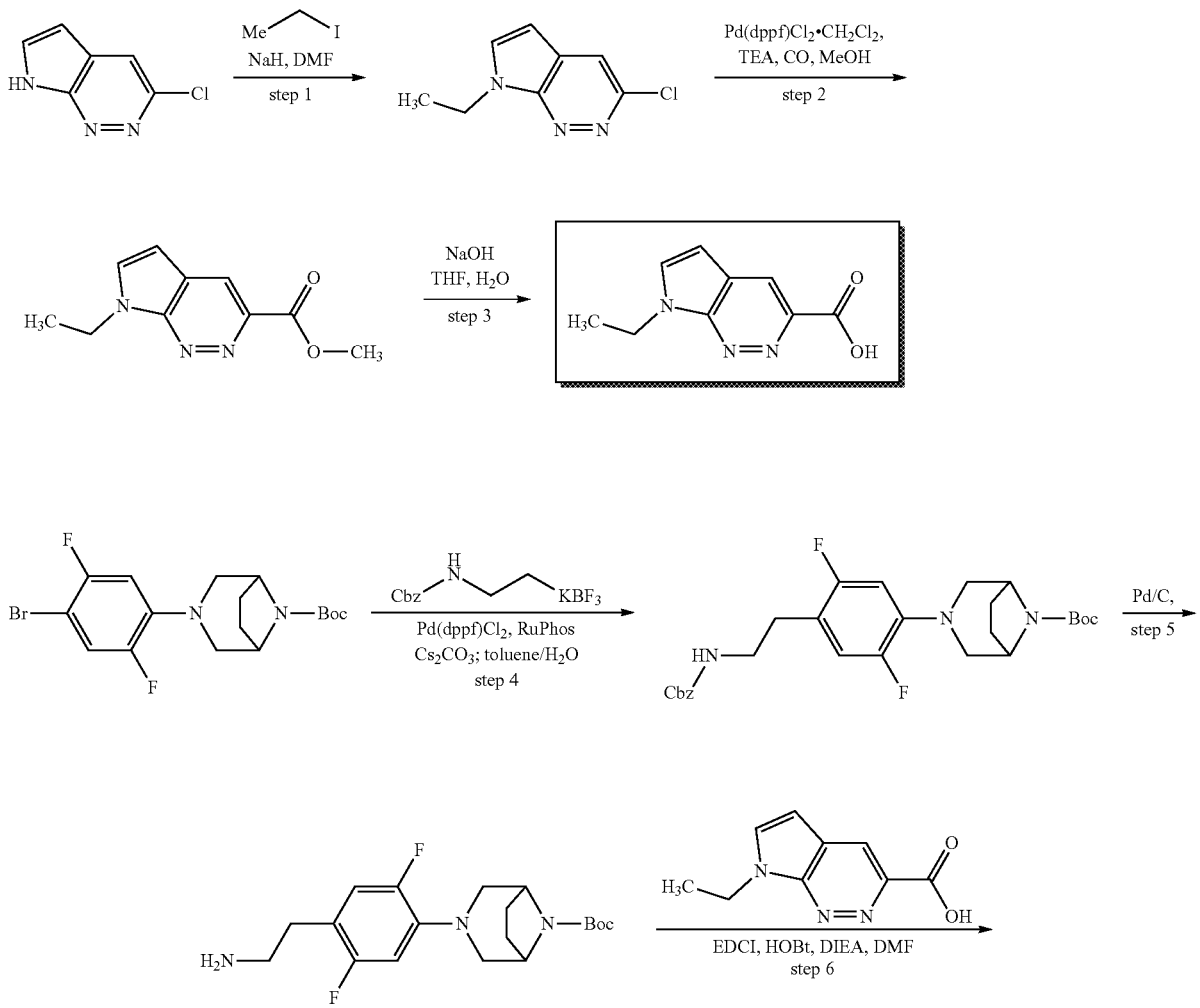

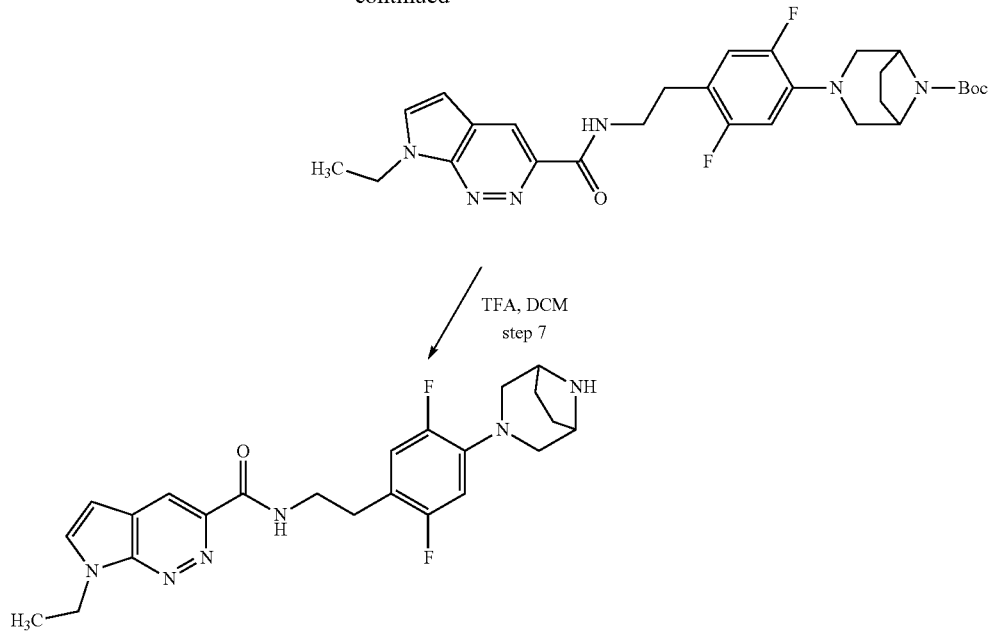

Step 1. 3-Chloro-7-ethyl-7H-pyrrolo[2,3-c]pyridazine

To a stirred solution of 3-chloro-7H-pyrrolo[2,3-c]pyridazine (0.300 g, 1.95 mmol) in N,N-dimethylformamide (8 mL) was added sodium hydride (0.197 g, 4.92 mmol; 60% dispersion) at 0° C. The reaction mixture was stirred for 30 min at 0° C. To this was added iodoethane (1.88 mL, 2.35 mmol). The resulting solution was stirred for 2 h at 25° C. The reaction was then quenched by the addition of NH$_4$Cl (sat.; 20 mL), then was extracted with ethyl acetate (3×20 mL). The organic layers were combined, dried over anhydrous sodium sulfate, filtered, and concentrated under vacuum to a residue that was purified by silica gel column chromatography (eluting with 1/1 ethyl acetate/petroleum ether) to afford 3-chloro-7-ethyl-7H-pyrrolo[2,3-c]pyridazine as a yellow oil. LCMS (ESI, m/z): 182, 184 [M+H]$^+$

Step 2. Methyl 7-ethyl-7H-pyrrolo[2,3-c]pyridazine-3-carboxylate]

Into a 50-mL pressure reactor was added a mixture of 3-chloro-7-ethyl-7H-pyrrolo[2,3-c]pyridazine (0.110 g, 0.604 mmol), Pd(dppf)Cl$_2$ (0.044 g, 0.060 mmol), TEA (1 mL), and methanol (20 mL). The resulting solution was stirred for 14 h at 120° C. in an oil bath under CO atmosphere (50 atm). After cooling to 25° C., the resulting mixture was concentrated under vacuum to a residue that was purified by silica gel column chromatography (eluting with 1/20-1/1 ethyl acetate/petroleum ether) to afford methyl 7-ethyl-7H-pyrrolo[2,3-c]pyridazine-3-carboxylate] as a yellow solid. LCMS (ESI, m/z): 206[M+H]$^+$

Step 3. 7-Ethyl-7H-pyrrolo[2,3-c]pyridazine-3-carboxylic acid

A solution of sodium hydroxide (0.098 g, 2.45 mmol) in water (5 mL) was added into a stirring solution of methyl 7-ethyl-7H-pyrrolo[2,3-c]pyridazine-3-carboxylate (0.100 g, 0.488 mmol) in methanol (5 mL). The resulting solution was stirred for 18 h at 25° C. The pH value of the solution was adjusted to 6 with hydrochloric acid (1N), then was concentrated under vacuum to a residue that was purified by a silica gel column chromatography (eluting with 10/1 dichloromethane/methanol) to afford 7-ethyl-7H-pyrrolo[2,3-c]pyridazine-3-carboxylic acid as a yellow solid. LCMS (ESI, m/z):192 [M+H]$^+$

Step 4. Tert-butyl 3-[4-(2-[[(benzyloxy)carbonyl]amino]ethyl)-2,5-difluorophenyl]-3,8-diazabicyclo[3.2.1]octane-8-carboxylate A mixture of tert-butyl 3-(4-bromo-2,5-difluorophenyl)-3,8-diazabicyclo[3.2.1]octane-8-carboxylate (14.0 g, 34.7 mmol), benzyl (2-(trifluoro-λ4-boraneyl)ethyl)carbamate, potassium salt (10.9 g, 38.2 mmol), Pd(dppf)Cl$_2$ (2.55 g, 3.49 mmol), RuPhos (3.25 g, 6.96 mmol), Cs$_2$CO$_3$ (22.7 g, 69.7 mmol), toluene (500 mL) and water (100 mL) under nitrogen was stirred for 3 h at 100° C. After cooling to 25° C. the resulting mixture was concentrated under vacuum to a residue that was purified by silica gel column chromatography (eluting with 1:5 ethyl acetate/petroleum ether) to afford tert-butyl 3-[4-(2-[[(benzyloxy)carbonyl]amino]ethyl)-2,5-difluorophenyl]-3,8-diazabicyclo[3.2.1]octane-8-carboxylate as a yellow oil. LCMS: (ESI, m/z): 502 [M+H]$^+$

Step 5. tert-Butyl 3-[4-(2-aminoethyl)-2,5-difluorophenyl]-3,8-diazabicyclo[3.2.1]octane-8-carboxylate A mixture of tert-butyl 3-[4-(2-[[(benzyloxy)carbonyl]amino]ethyl)-2,5-difluorophenyl]-3,8-diazabicyclo[3.2.1]octane-8-carboxylate (12.0 g, 23.9 mmol) and palladium on carbon (12.0 g, 10%) in ethyl acetate (500 mL) was stirred for 1 h at 20° C. under a hydrogen atmosphere (balloon). The solids were removed by filtration over Celite, and the filtrate was concentrated under vacuum to a residue that was purified by silica gel column chromatography (eluting with 10:1 dichloromethane/methanol) to afford tert-butyl 3-[4-(2- aminoethyl)-2,5-difluorophenyl]-3,8-diazabicyclo[3.2.1]octane-8-carboxylate as a light yellow oil. LCMS: (ESI, m/z): 368 [M+H]+

Step 6. tert-Butyl 3-[4-[2-([7-ethyl-7H-pyrrolo[2,3-c]pyridazin-3-yl]formamido)ethyl]-2,5-difluorophenyl]-3,8-diazabicyclo[3.2.1]octane-8-carboxylate A solution of 7-ethyl-7H-pyrrolo[2,3-c]pyridazine-3-carboxylic acid (0.30 g, 0.159 mmol), tert-butyl 3-[4-(2-aminoethyl)-2,5-difluorophenyl]-3,8-diazabicyclo[3.2.1]octane-8-carboxylate (0.070 g, 0.190 mmol), EDCI (0.039 g, 0.200 mmol), HOBT (0.026 g, 0.190 mmol), and DIEA (0.130 mL, 0.320 mmol) in N,N-dimethylformamide (5 mL) was stirred for 18 h at 25° C. The resulting mixture was diluted with H$_2$O (10 mL), then was extracted with ethyl acetate (3×20 mL). The organic layers were combined, dried over anhydrous sodium sulfate, filtered, and concentrated under vacuum to a residue that was purified by silica gel column chromatography (eluting with 1/10-1/1 ethyl acetate/petroleum ether) to afford tert-butyl 3-[4-[2-([7-ethyl-7H-pyrrolo[2,3-c]pyridazin-3-yl]formamido)ethyl]-2,5-difluorophenyl]-3,8-diazabicyclo[3.2.1]octane-8-carboxylate as a white solid. LCMS (ESI, m/z): 541 [M+H]+

Step 7. N-[2-(4-[3,8-diazabicyclo[3.2.1]octan-3-yl]-2,5-difluorophenyl)ethyl]-7-ethyl-7H-pyrrolo[2,3-c]pyridazine-3-carboxamide A solution of tert-butyl 3-[4-[2-([7-ethyl-7H-pyrrolo[2,3-c]pyridazin-3-yl]formamido)ethyl]-2,5-difluorophenyl]-3,8-diazabicyclo[3.2.1]octane-8-carboxylate (0.022 mg, 0.041 mmol) and trifluoroacetic acid (1 mL) in dichloromethane (5 mL) was stirred for 30 min at 20° C. The resulting mixture was concentrated under vacuum to a residue that was taken up into DCM (5 mL). The pH value was adjusted to 8 with a solution of NH$_3$ (7 M) in MeOH, and the resulting mixture was concentrated under vacuum to a residue that was purified by Prep-HPLC (Column: XBridge BEH C18 OBD Prep Column, 130 Å, 5 µm, 19 mm×150 mm; Mobile phase, A: water (containing 0.05% NH$_3$H$_2$O) and B: MeCN (30% up to 45% over 8 min); Flow rate: 20 mL/min; Detector: 254 & 220 nm) to afford N-[2-(4-[3,8-diazabicyclo[3.2.1]octan-3-yl]-2,5-difluorophenyl)ethyl]-7-ethyl-7H-pyrrolo[2,3-c]pyridazine-3-carboxamide as a white solid.

$^1$H-NMR (CD$_3$OD, 300 MHz) δ (ppm): 8.43 (s, 1H), 7.86 (d, J=3.6 Hz, 1H), 7.01-6.94 (m, 1H), 6.71 (d, J=3.3 Hz, 1H), 6.66-6.59 (m, 1H), 4.54 (q, J=7.2 Hz, 2H), 3.70-3.64 (m, 2H), 3.56-3.53 (m, 2H), 3.29-3.17 (m, 2H), 2.93-2.84 (m, 4H), 2.04-1.96 (m, 2H), 1.87-1.78 (m, 2H), 1.58-1.46 (t, J=7.2 Hz, 3H). LCMS (ES, m/z): 441[M+H]+

The compounds in Table 4 can be prepared using the methods described for Examples 2-1, 2-2, and 4-1.

TABLE 4

| Ex. # | Structure and Compound Name | LRMS m/z [M + H]+ | $^1$H NMR | Assay A-1(a) | Assay A-1(b) | Assay A-2 |
|---|---|---|---|---|---|---|
| 4-1 | | 441 | see above | ++++ | +++ | ++ |

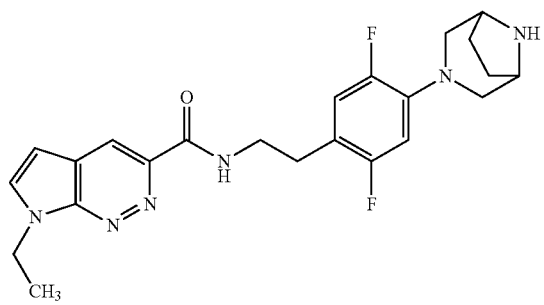

N-(4-(3,8-diazabicyclo[3.2.1]octan-3-yl)-2,5-difluorophenethyl)-7-ethyl-7H-pyrrolo[2,3-b]pyridazine-3-carboxamide TABLE 4-continued

| Ex. # | Structure and Compound Name | LRMS m/z [M + H]+ | 1H NMR | Assay A-1(a) | Assay A-1(b) | Assay A-2 |
|---|---|---|---|---|---|---|
| 4-2 | 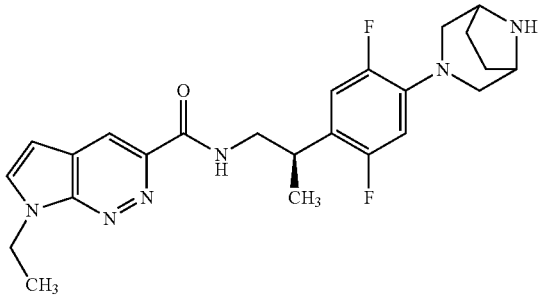<br>N-((2R)-2-(4-(3,8-diazabicyclo[3.2.1]octan-3-yl)-2,5-difluorophenyl)propyl)-7-ethyl-7H-pyrrolo[2,3-c]pyridazine-3-carboxamide | 455 | (CD$_3$OD, 400 MHz) δ (ppm): 8.66 (s, 1H), 8.36 (s, 1H), 7.56 (d, J = 3.6 Hz, 1H), 7.06 (q, J = 6.8 Hz, 1H), 6.72 (d, J = 2.0 Hz, 1H), 6.62 (dd, J = 12.0, 7.6 Hz, 1H), 4.55 (q, J = 7.2 Hz, 2H), 3.73-3.68 (m, 1H), 3.64-3.59 (m, 3H), 3.48-3.38 (m, 1H), 3.30-3.21 (m, 2H), 2.91-2.88 (m, 2H), 2.03-1.98 (m, 2H), 1.89-1.85 (m, 2H), 1.54 (t, J = 7.2 Hz, 3H), 1.30 (t, J = 7.2 Hz, 3H) | +++ | ++ | ++ |
| 4-3 | 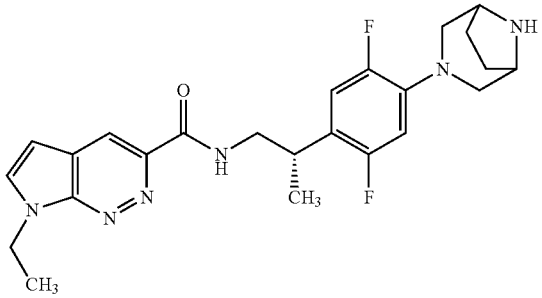<br>N-((2S)-2-(4-(3,8-diazabicyclo[3.2.1]octan-3-yl)-2,5-difluorophenyl)propyl)-7-ethyl-7H-pyrrolo[2,3-c]pyridazine-3-carboxamide | 455 | (CD$_3$OD, 400 MHz) δ (ppm): 8.66 (s, 1H), 8.36 (s, 1H), 7.56 (d, J = 3.6 Hz, 1H), 7.06 (q, J = 6.8 Hz, 1H), 6.72 (d, J = 3.6 Hz, 1H), 6.62 (dd, J = 11.6, 7.2 Hz, 1H), 4.55 (q, J = 7.2 Hz, 2H), 3.73-3.68 (m, 1H), 3.64-3.59 (m, 3H), 3.48-3.38 (m, 1H), 3.30-3.21 (m, 2H), 2.91-2.88 (m, 2H), 2.03-1.98 (m, 2H), 1.89-1.86 (m, 2H), 1.54 (t, J = 7.2 Hz, 3H), 1.32 (t, J = 7.2 Hz, 3H) | +++ | ++ | ++ |
| 4-4 | 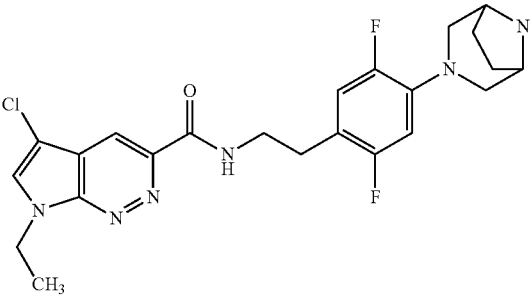<br>N-(4-(3,8-diazabicyclo[3.2.1]octan-3-yl)-2,5-difluorophenethyl)-5-chloro-7-ethyl-7H-pyrrolo[2,3-c]pyridazine-3-carboxamide | 475, 477 | (CD$_3$OD, 400 MHz) δ (ppm): 8.41 (s, 1H), 8.01 (s, 1H), 6.99 (q, J = 6.8 Hz, 1H), 6.63 (dd, J = 11.6, 6.8 Hz, 1H), 4.59 (q, J = 7.2 Hz, 2H), 3.70 (q, J = 7.2 Hz, 2H), 3.51-3.49 (m, 2H), 3.21-3.18 (m, 2H), 2.95-2.86 (m, 4H), 1.99-1.94 (m, 2H), 1.87-1.81 (m, 2H), 1.55 (t, J = 7.2 Hz, 3H) | ++++ | +++ | +++ |

What is claimed is:
1. A compound of Formula (I):

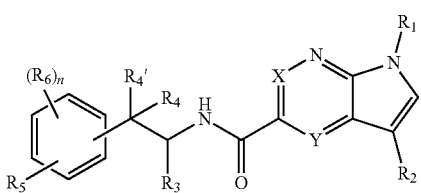

or pharmaceutically acceptable form thereof, wherein:
X is selected from N or C(R');
R' is selected from hydrogen, deuterium, and $CH_3$;
Y is C(R);
R is selected from hydrogen, $NH_2$, and C1-C4 alkyl groups;
$R_1$ is selected from Rx, hydrogen, C1-C5 linear and C3-C5 branched alkyl groups, wherein the alkyl groups are optionally substituted with one or more Rx;
each Rx is selected from halogen or —OH;
$R_2$ is selected from hydrogen and halogen;
$R_3$, $R_4$, and $R_{4'}$ are each independently selected from hydrogen and C1-C4 alkyl;
$R_5$ is a 6- to 8-membered heterocyclic ring;
$R_6$ is selected from hydrogen, deuterium, halogen, C1-C4 alkyl, and —CN; and
n is 0, 1, or 2.

2. The compound of claim 1, wherein:
X is C(R');
R' is selected from hydrogen and deuterium;
R is $NH_2$;
$R_1$, $R_2$, $R_3$, $R_4$, and $R_{4'}$ are hydrogen;
$R_5$ is a 6-membered heterocyclic ring; and
n is 0.

3. The compound of claim 1, wherein:
X is C(R');
R' is selected from hydrogen and deuterium;
R is hydrogen;
$R_1$ is C1-C3 linear alkyl, optionally substituted with one to three Rx;
$R_2$ and $R_3$ are hydrogen;
$R_4$ and $R_{4'}$ are independently selected from hydrogen and $CH_3$;
$R_5$ is a 6-8-membered heterocyclic ring;
$R_6$ is selected from hydrogen, deuterium, and halogen; and
n is 0, 1, or 2.

4. The compound of claim 1, wherein:
X is C(R'), wherein R' is hydrogen;
R is hydrogen;
$R_1$ is methyl or ethyl, optionally substituted with one to three Rx;
$R_2$ and $R_3$ are hydrogen;
$R_4$ and $R_{4'}$ are independently selected from hydrogen and $CH_3$;
$R_5$ is a 6-8-membered heterocyclic ring;
$R_6$ is selected from hydrogen and halogen; and
n is 0, 1, or 2.

5. The compound of claim 1, wherein:
X is C(R');
R' is selected from hydrogen and deuterium;
R is hydrogen;
$R_1$ is C3-C4 branched alkyl optionally substituted with one to three Rx;
$R_2$ and $R_3$ are hydrogen;
$R_4$ and $R_{4'}$ are independently selected from hydrogen and $CH_3$;
$R_5$ is a 6-8-membered heterocyclic ring;
$R_6$ is selected from hydrogen, deuterium, and halogen; and
n is 0, 1, or 2.

6. The compound of claim 1, wherein:
X is C(R'), wherein R' is hydrogen;
R is hydrogen;
$R_1$ is C3-C4 branched alkyl, optionally substituted with one to three Rx;
$R_2$ and $R_3$ are hydrogen;
$R_4$ and $R_{4'}$ are hydrogen;
$R_5$ is a 6-8-membered heterocyclic ring;
$R_6$ is selected from hydrogen and halogen; and
n is 0, 1, or 2.

7. The compound of claim 1, wherein:
X is C(R'), wherein R' is hydrogen;
R is hydrogen;
$R_1$ is hydrogen;
$R_2$ is halogen;
$R_3$ is hydrogen;
$R_4$ and $R_{4'}$ are hydrogen;
$R_5$ is a 6-8-membered heterocyclic ring;
$R_6$ is selected from hydrogen and halogen; and
n is 0, 1, or 2.

8. The compound of claim 1, wherein:
X is C(R'), wherein R' is hydrogen;
R is hydrogen;
$R_1$ is selected from hydrogen, and C1-C3 linear alkyl optionally substituted with one to three Rx;
$R_2$ is halogen;
$R_3$ is hydrogen;
$R_4$ and $R_{4'}$ are hydrogen;
$R_5$ is a 6-8-membered heterocyclic ring;
$R_6$ is selected from hydrogen and halogen; and
n is 0, 1, or 2.

9. The compound of claim 1, wherein:
X is N;
R is hydrogen;
$R_1$ is selected from hydrogen, and C1-C3 linear alkyl optionally substituted with one to three Rx;
$R_2$ is hydrogen;
$R_3$ is hydrogen;
$R_4$ and $R_{4'}$ are selected from hydrogen and $CH_3$;
$R_5$ is a 6-8-membered heterocyclic ring;
$R_6$ is selected from hydrogen and halogen; and
n is 0, 1, or 2.

10. The compound of claim 1, wherein R5 is a 6-8 membered heterocyclic ring with two nitrogens.

11. The compound of claim 1, wherein each halogen is independently selected from F and Cl.

12. The compound of claim 1, wherein the compound is chosen from:

| Ex. # | Structure | Compound Name |
|---|---|---|
| 1-1 | 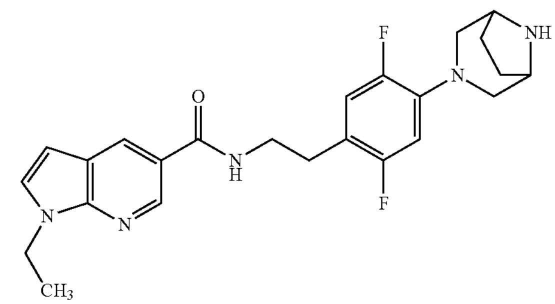 [SMILES: CCn1ccc2cc(C(=O)NCCc3cc(F)c(N4CC5CCC(C4)N5)cc3F)cnc21] | N-(4-(3,8-diazabicyclo[3.2.1]octan-3-yl)-2,5-difluorophenethyl)-1-ethyl-1H-pyrrolo[2,3-b]pyridine-5-carboxamide |
| 1-2 | 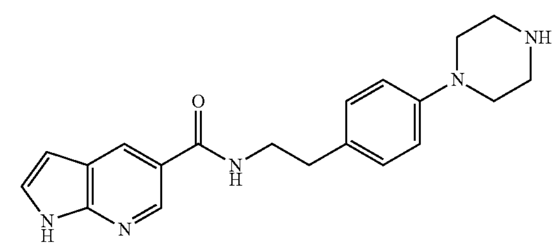 [SMILES: O=C(NCCc1ccc(N2CCNCC2)cc1)c1cnc2[nH]ccc2c1] | N-(4-(piperazin-1-yl)phenethyl)-1H-pyrrolo[2,3-b]pyridine-5-carboxamide |
| 1-3 | 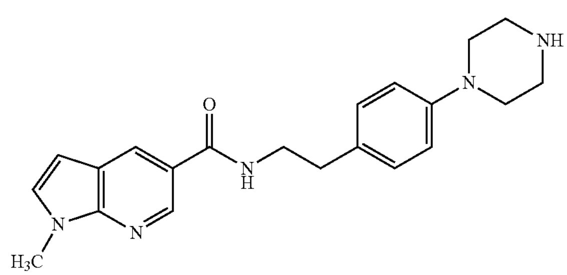 [SMILES: Cn1ccc2cc(C(=O)NCCc3ccc(N4CCNCC4)cc3)cnc21] | 1-methyl-N-(4-(piperazin-1-yl)phenethyl)-1H-pyrrolo[2,3-b]pyridine-5-carboxamide |
| 1-4 | 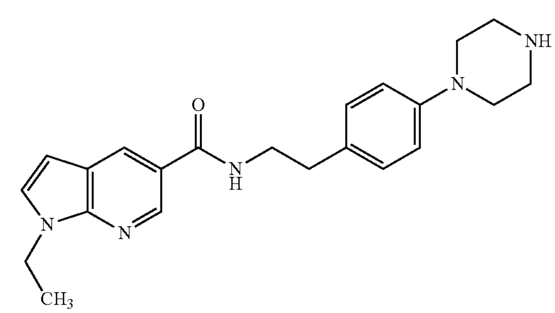 [SMILES: CCn1ccc2cc(C(=O)NCCc3ccc(N4CCNCC4)cc3)cnc21] | 1-ethyl-N-(4-(piperazin-1-yl)phenethyl)-1H-pyrrolo[2,3-b]pyridine-5-carboxamide |
| 1-5 | 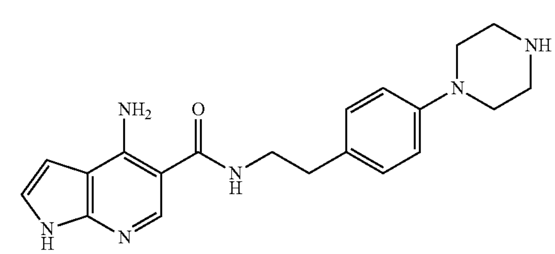 [SMILES: Nc1c(C(=O)NCCc2ccc(N3CCNCC3)cc2)cnc2[nH]ccc12] | 4-amino-N-(4-(piperazin-1-yl)phenethyl)-1H-pyrrolo[2,3-b]pyridine-5-carboxamide |

-continued

| Ex. # | Structure | Compound Name |
|---|---|---|
| 1-6 | 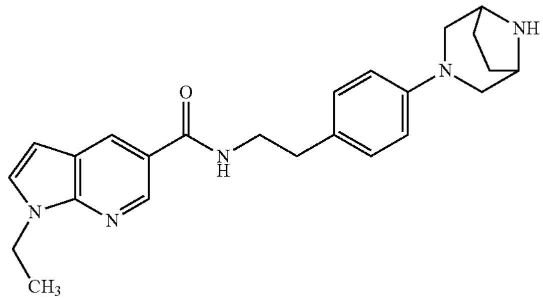 [SMILES: CCn1ccc2cc(C(=O)NCCc3ccc(N4CC5CCC(C4)N5)cc3)cnc21] | N-(4-(3,8-diazabicyclo[3.2.1]octan-3-yl)phenethyl)-1-ethyl-1H-pyrrolo[2,3-b]pyridine-5-carboxamide |
| 1-7 | 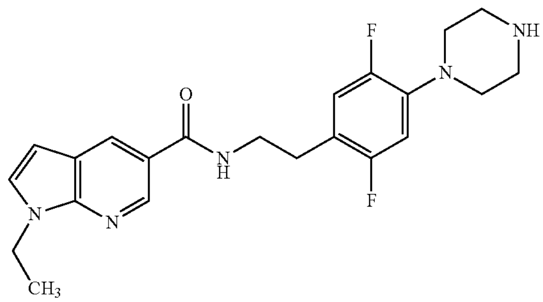 [SMILES: CCn1ccc2cc(C(=O)NCCc3cc(F)c(N4CCNCC4)cc3F)cnc21] | N-(2,5-difluoro-4-(piperazin-1-yl)phenethyl)-1-ethyl-1H-pyrrolo[2,3-b]pyridine-5-carboxamide |
| 1-8 | 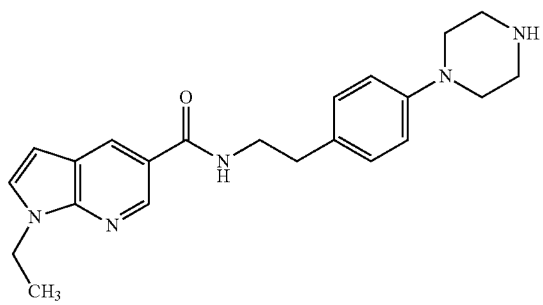 [SMILES: CCn1ccc2cc(C(=O)NCCc3ccc(N4CCNCC4)cc3)cnc21] | N-(4-(piperazin-1-yl)phenethyl)-1-(2,2,2-trifluoroethyl)-1H-pyrrolo[2,3-b]pyridine-5-carboxamide |
| 1-9 | 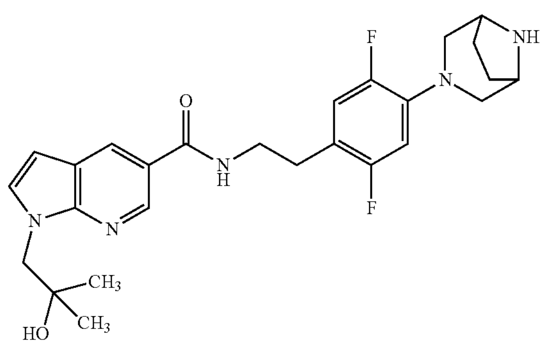 [SMILES: CC(C)(O)Cn1ccc2cc(C(=O)NCCc3cc(F)c(N4CC5CCC(C4)N5)cc3F)cnc21] | N-(4-(3,8-diazabicyclo[3.2.1]octan-3-yl)-2,5-difluorophenethyl)-1-(2-hydroxy-2-methylpropyl)-1H-pyrrolo[2,3-b]pyridine-5-carboxamide |
| 1-10 | 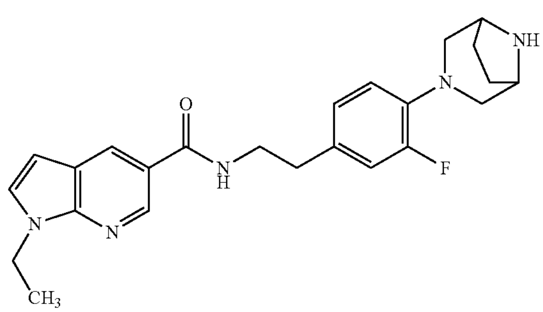 [SMILES: CCn1ccc2cc(C(=O)NCCc3ccc(N4CC5CCC(C4)N5)c(F)c3)cnc21] | N-(4-(3,8-diazabicyclo[3.2.1]octan-3-yl)-3-fluorophenethyl)-1-ethyl-1H-pyrrolo[2,3-b]pyridine-5-carboxamide |

-continued

| Ex. # | Structure | Compound Name |
|---|---|---|
| 2-1 | 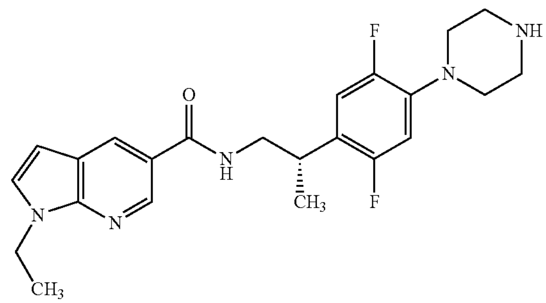 [SMILES: CCn1ccc2cc(C(=O)NC[C@@H](C)c3cc(F)c(N4CCNCC4)cc3F)cnc21] | (S)-N-(2-(2,5-difluoro-4-(piperazin-1-yl)phenyl)propyl)-1-ethyl-1H-pyrrolo[2,3-b]pyridine-5-carboxamide |
| 2-2 | 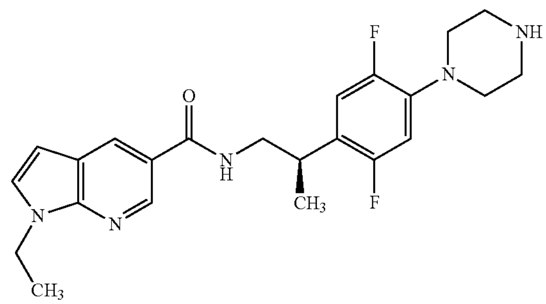 [SMILES: CCn1ccc2cc(C(=O)NC[C@H](C)c3cc(F)c(N4CCNCC4)cc3F)cnc21] | (R)-N-(2-(2,5-difluoro-4-(piperazin-1-yl)phenyl)propyl)-1-ethyl-1H-pyrrolo[2,3-b]pyridine-5-carboxamide |
| 2-3 | 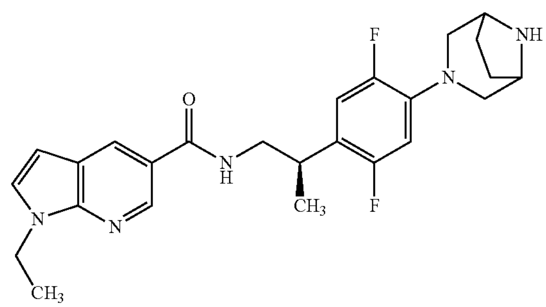 [SMILES: CCn1ccc2cc(C(=O)NC[C@H](C)c3cc(F)c(N4CC5CCC(C4)N5)cc3F)cnc21] | N-((2R)-2-(4-(3,8-diazabicyclo[3.2.1]octan-3-yl)-2,5-difluorophenyl)propyl)-1-ethyl-1H-pyrrolo[2,3-b]pyridine-5-carboxamide |
| 2-4 | 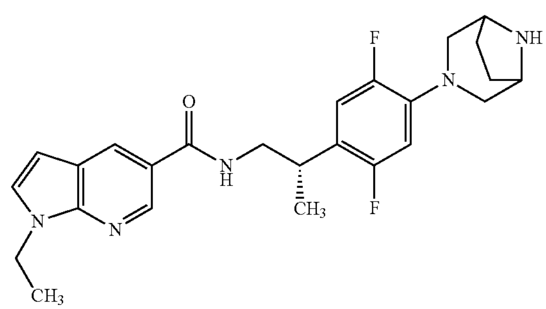 [SMILES: CCn1ccc2cc(C(=O)NC[C@@H](C)c3cc(F)c(N4CC5CCC(C4)N5)cc3F)cnc21] | N-((2S)-2-(4-(3,8-diazabicyclo[3.2.1]octan-3-yl)-2,5-difluorophenyl)propyl)-1-ethyl-1H-pyrrolo[2,3-b]pyridine-5-carboxamide |
| 3-1 | 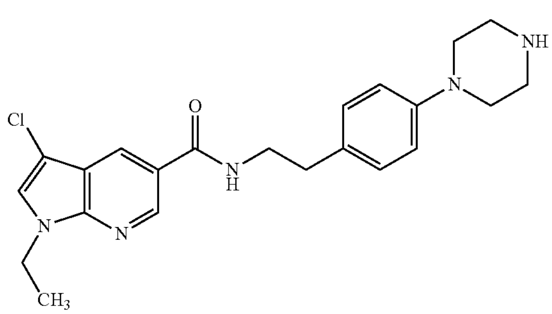 [SMILES: CCn1cc(Cl)c2cc(C(=O)NCCc3ccc(N4CCNCC4)cc3)cnc21] | 3-chloro-1-ethyl-N-(4-(piperazin-1-yl)phenethyl)-1H-pyrrolo[2,3-b]pyridine-5-carboxamide |

-continued

| Ex. # | Structure | Compound Name |
|---|---|---|
| 3-2 | 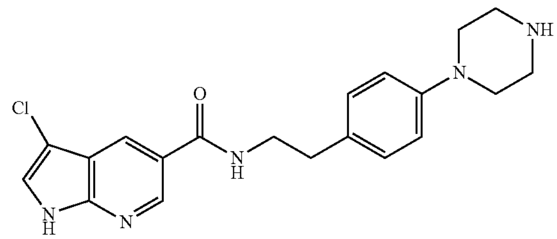 [SMILES: O=C(NCCc1ccc(N2CCNCC2)cc1)c1cnc2[nH]cc(Cl)c2c1] | 3-chloro-N-(4-(piperazin-1-yl)phenethyl)-1H-pyrrolo[2,3-b]pyridine-5-carboxamide |
| 4-1 | 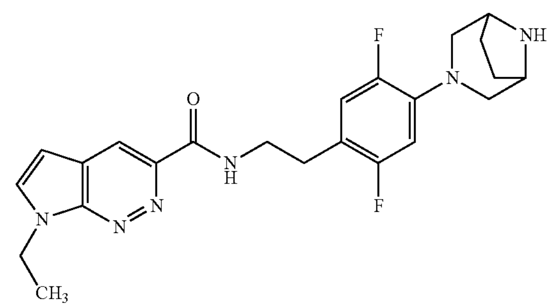 [SMILES: CCn1ccc2cc(C(=O)NCCc3cc(F)c(N4CC5CCC(C4)N5)cc3F)nnc21] | N-(4-(3,8-diazabicyclo[3.2.1]octan-3-yl)-2,5-difluorophenethyl)-7-ethyl-7H-pyrrolo[2,3-c]pyridazine-3-carboxamide |
| 4-2 | 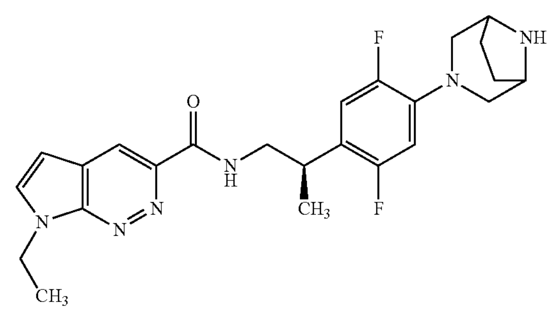 [SMILES: CCn1ccc2cc(C(=O)NC[C@H](C)c3cc(F)c(N4CC5CCC(C4)N5)cc3F)nnc21] | N-((2R)-2-(4-(3,8-diazabicyclo[3.2.1]octan-3-yl)-2,5-difluorophenyl)propyl)-7-ethyl-7H-pyrrolo[2,3-c]pyridazine-3-carboxamide |
| 4-3 | 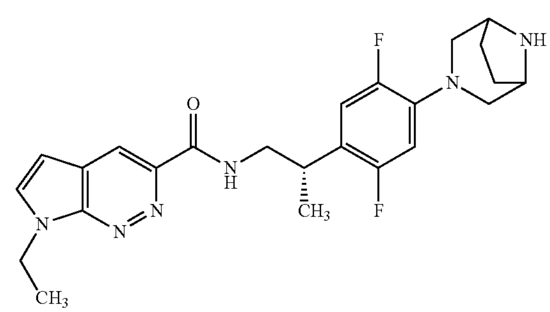 [SMILES: CCn1ccc2cc(C(=O)NC[C@@H](C)c3cc(F)c(N4CC5CCC(C4)N5)cc3F)nnc21] | N-((2S)-2-(4-(3,8-diazabicyclo[3.2.1]octan-3-yl)-2,5-difluorophenyl)propyl)-7-ethyl-7H-pyrrolo[2,3-c]pyridazine-3-carboxamide |
| 4-4 | | N-(4-(3,8-diazabicyclo[3.2.1]octan-3-yl)-2,5-difluorophenethyl)-5-chloro-7-ethyl-7H-pyrrolo[2,3-c]pyridazine-3-carboxamide | and;
wherein the compound is:
 (a) a USP28 Inhibitor compound having an $IC_{50}$ of 0.001-10 micromolar in the Ubiquitin-Rhodamine 110 Assay for USP28;
 (b) a USP25 Inhibitor compound having an $IC_{50}$ of 0.001-10 micromolar in the Ubiquitin-Rhodamine 110 Assay for USP25.

13. The compound of claim 12, wherein the compound is
 (c) a USP28 Inhibitor compound having an $IC_{50}$ of 0.001-2 micromolar in the Ubiquitin-Rhodamine 110 Assay for USP28;
 (d) a USP25 Inhibitor compound having an $IC_{50}$ of 0.001-2 micromolar in the Ubiquitin-Rhodamine 110 Assay for USP25.

14. The compound of claim 1, chosen from:

| Ex. # | Structure | Compound Name |
|---|---|---|
| 1-1 | 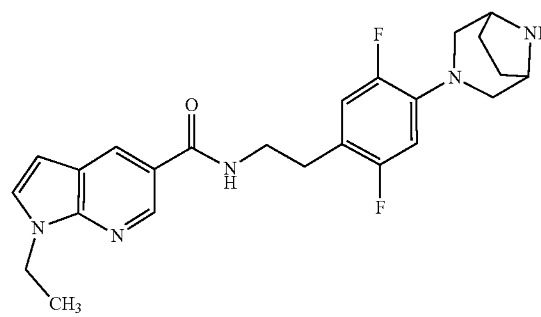 | N-(4-(3,8-diazabicyclo[3.2.1]octan-3-yl)-2,5-difluorophenethyl)-1-ethyl-1H-pyrrolo[2,3-b]pyridine-5-carboxamide |
| 1-2 | 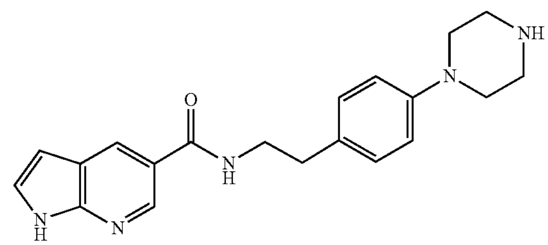 [SMILES: O=C(NCCc1ccc(N2CCNCC2)cc1)c1cnc2[nH]ccc2c1] | N-(4-(piperazin-1-yl)phenethyl)-1H-pyrrolo[2,3-b]pyridine-5-carboxamide |
| 1-3 | 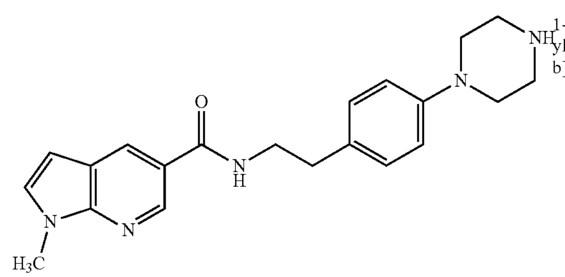 | 1-methyl-N-(4-(piperazin-1-yl)phenethyl)-1H-pyrrolo[2,3-b]pyridine-5-carboxamide |
| 1-4 | 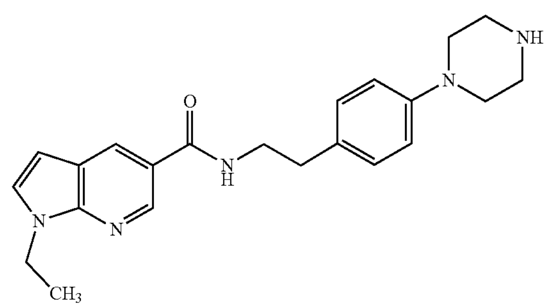 | 1-ethyl-N-(4-(piperazin-1-yl)phenethyl)-1H-pyrrolo[2,3-b]pyridine-5-carboxamide |
| 1-5 | 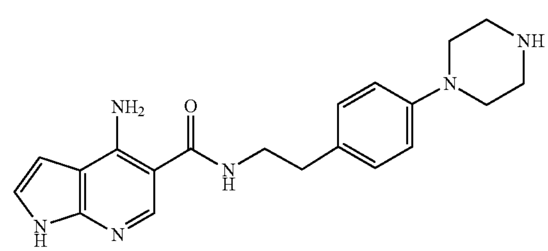 [SMILES: Nc1c(C(=O)NCCc2ccc(N3CCNCC3)cc2)cnc2[nH]ccc12] | 4-amino-N-(4-(piperazin-1-yl)phenethyl)-1H-pyrrolo[2,3-b]pyridine-5-carboxamide |

| Ex. # | Structure | Compound Name |
| --- | --- | --- |
| 1-6 | 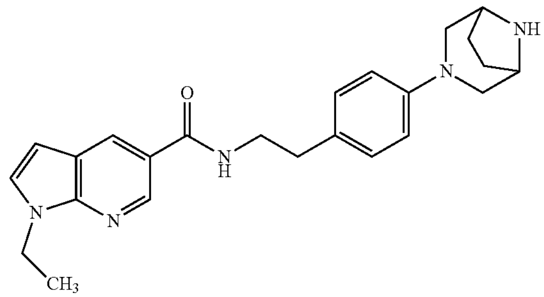 [SMILES: CCn1ccc2cc(C(=O)NCCc3ccc(N4CC5CCC(C4)N5)cc3)cnc21] | N-(4-(3,8-diazabicyclo[3.2.1]octan-3-yl)phenethyl)-1-ethyl-1H-pyrrolo[2,3-b]pyridine-5-carboxamide |
| 1-7 | 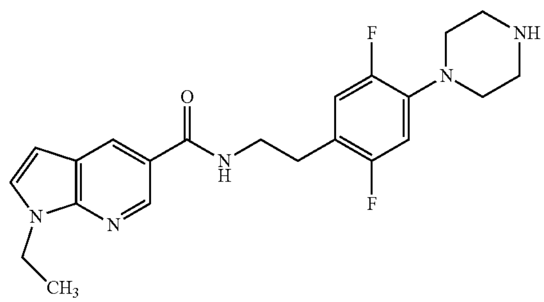 [SMILES: CCn1ccc2cc(C(=O)NCCc3cc(F)c(N4CCNCC4)cc3F)cnc21] | N-(2,5-difluoro-4-(piperazin-1-yl)phenethyl)-1-ethyl-1H-pyrrolo[2,3-b]pyridine-5-carboxamide |
| 1-8 | 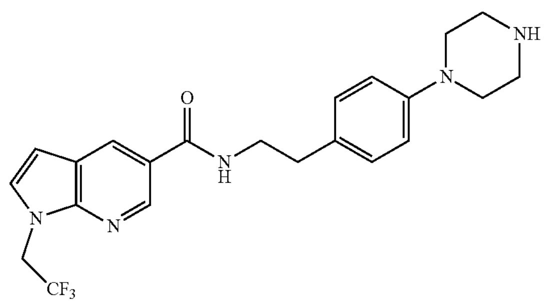 [SMILES: O=C(NCCc1ccc(N2CCNCC2)cc1)c1cnc2c(ccn2CC(F)(F)F)c1] | N-(4-(piperazin-1-yl)phenethyl)-1-(2,2,2-trifluoroethyl)-1H-pyrrolo[2,3-b]pyridine-5-carboxamide |
| 1-9 | 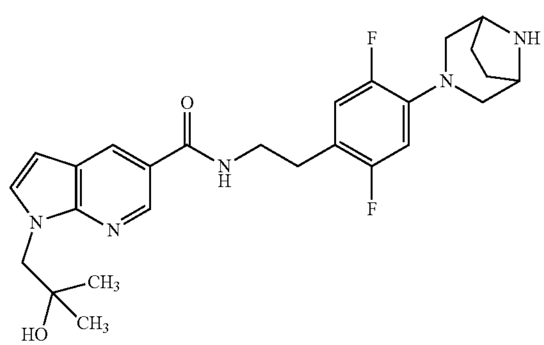 [SMILES: CC(C)(O)Cn1ccc2cc(C(=O)NCCc3cc(F)c(N4CC5CCC(C4)N5)cc3F)cnc21] | N-(4-(3,8-diazabicyclo[3.2.1]octan-3-yl)-2,5-difluorophenethyl)-1-(2-hydroxy-2-methylpropyl)-1H-pyrrolo[2,3-b]pyridine-5-carboxamide |
| 1-10 | 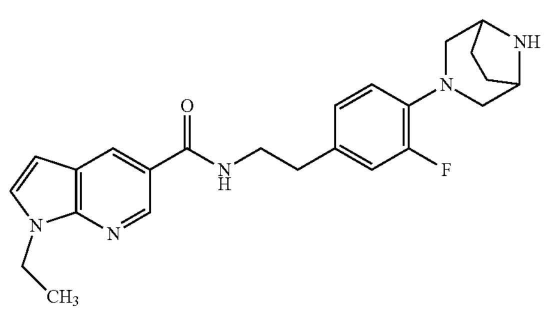 [SMILES: CCn1ccc2cc(C(=O)NCCc3ccc(N4CC5CCC(C4)N5)c(F)c3)cnc21] | N-(4-(3,8-diazabicyclo[3.2.1]octan-3-yl)-3-fluorophenethyl)-1-ethyl-1H-pyrrolo[2,3-b]pyridine-5-carboxamide |

| Ex. # | Structure | Compound Name |
|---|---|---|
| 2-1 | 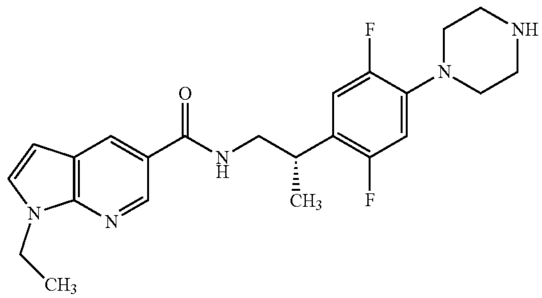 [SMILES: CCn1ccc2cc(C(=O)NC[C@@H](C)c3cc(F)c(N4CCNCC4)cc3F)cnc21] | (S)-N-(2-(2,5-difluoro-4-(piperazin-1-yl)phenyl)propyl)-1-ethyl-1H-pyrrolo[2,3-b]pyridine-5-carboxamide |
| 2-2 | 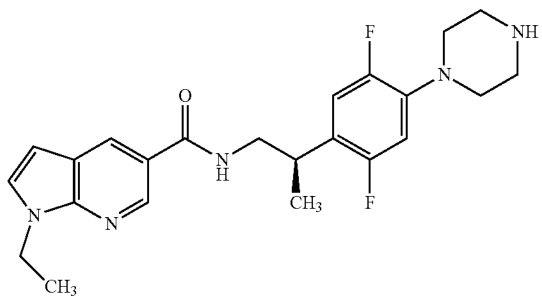 [SMILES: CCn1ccc2cc(C(=O)NC[C@H](C)c3cc(F)c(N4CCNCC4)cc3F)cnc21] | (R)-N-(2-(2,5-difluoro-4-(piperazin-1-yl)phenyl)propyl)-1-ethyl-1H-pyrrolo[2,3-b]pyridine-5-carboxamide |
| 2-3 | 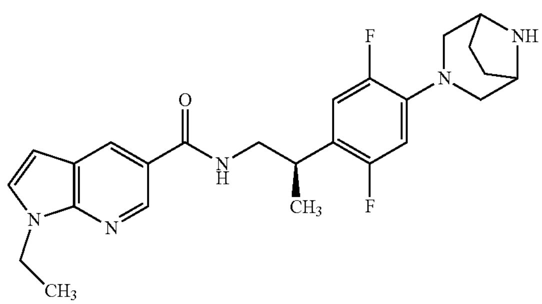 [SMILES: CCn1ccc2cc(C(=O)NC[C@H](C)c3cc(F)c(N4CC5CCC(C4)N5)cc3F)cnc21] | N-((2R)-2-(4-(3,8-diazabicyclo[3.2.1]octan-3-yl)-2,5-difluorophenyl)propyl)-1-ethyl-1H-pyrrolo[2,3-b]pyridine-5-carboxamide |
| 2-4 | 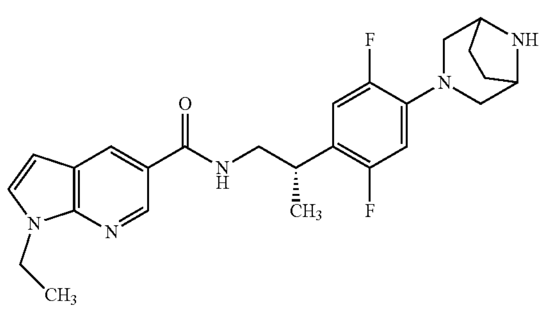 [SMILES: CCn1ccc2cc(C(=O)NC[C@@H](C)c3cc(F)c(N4CC5CCC(C4)N5)cc3F)cnc21] | N-((2S)-2-(4-(3,8-diazabicyclo[3.2.1]octan-3-yl)-2,5-difluorophenyl)propyl)-1-ethyl-1H-pyrrolo[2,3-b]pyridine-5-carboxamide |
| 3-1 | 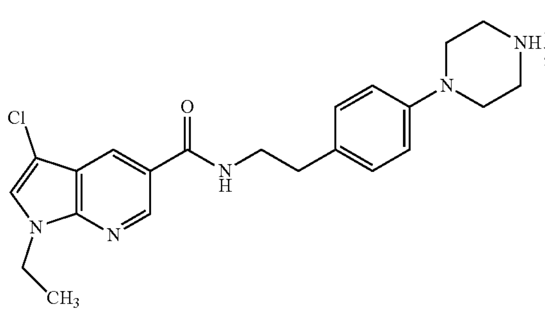 | 3-chloro-1-ethyl-N-(4-(piperazin-1-yl)phenethyl)-1H-pyrrolo[2,3-b]pyridine-5-carboxamide |

| Ex. # | Structure | Compound Name |
|---|---|---|
| 3-2 | 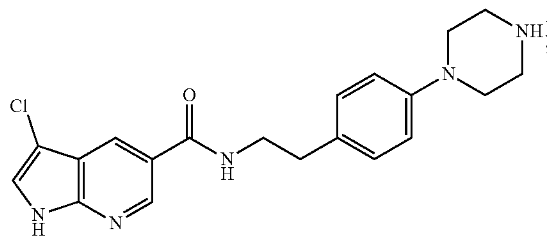 | 3-chloro-N-(4-(piperazin-1-yl)phenethyl)-1H-pyrrolo[2,3-b]pyridine-5-carboxamide |
| 4-1 | 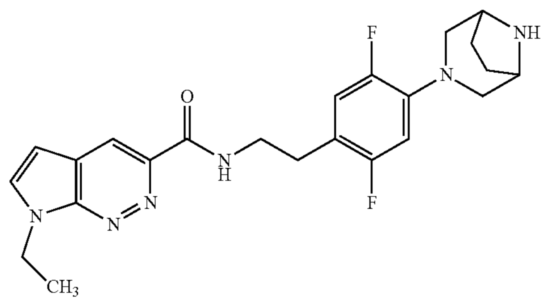 [SMILES: CCn1ccc2cc(C(=O)NCCc3cc(F)c(N4CC5CCC(C4)N5)cc3F)nnc21] | N-(4-(3,8-diazabicyclo[3.2.1]octan-3-yl)-2,5-difluorophenethyl)-7-ethyl-7H-pyrrolo[2,3-c]pyridazine-3-carboxamide |
| 4-2 | 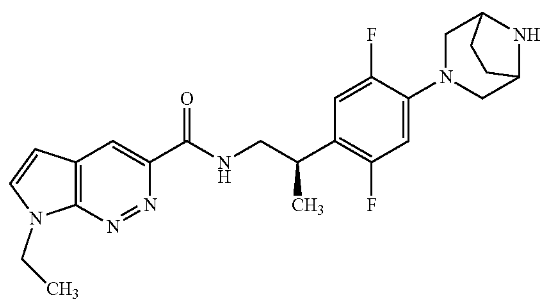 [SMILES: CCn1ccc2cc(C(=O)NC[C@H](C)c3cc(F)c(N4CC5CCC(C4)N5)cc3F)nnc21] | N-((2R)-2-(4-(3,8-diazabicyclo[3.2.1]octan-3-yl)-2,5-difluorophenyl)propyl)-7-ethyl-7H-pyrrolo[2,3-c]pyridazine-3-carboxamide |
| 4-3 | 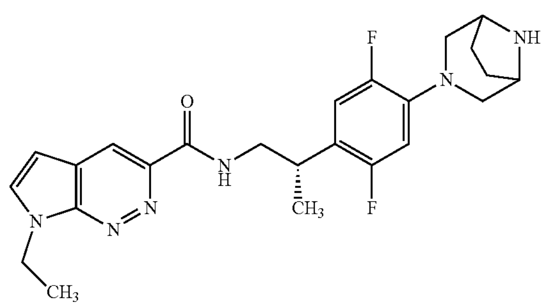 [SMILES: CCn1ccc2cc(C(=O)NC[C@@H](C)c3cc(F)c(N4CC5CCC(C4)N5)cc3F)nnc21] | N-((2S)-2-(4-(3,8-diazabicyclo[3.2.1]octan-3-yl)-2,5-difluorophenyl)propyl)-7-ethyl-7H-pyrrolo[2,3-c]pyridazine-3-carboxamide |
| 4-4 | 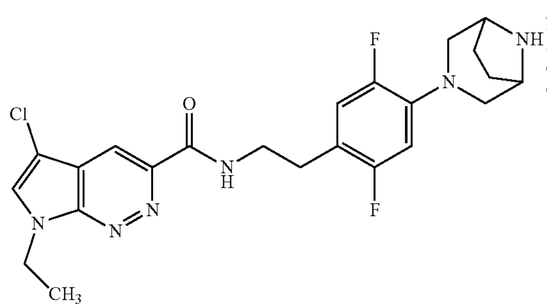 | N-(4-(3,8-diazabicyclo[3.2.1]octan-3-yl)-2,5-difluorophenethyl)-5-chloro-7-ethyl-7H-pyrrolo[2,3-c]pyridazine-3-carboxamide |

15. A composition comprising at least one compound of claim 1, and a biologically acceptable carrier.

\* \* \* \* \*